(12) United States Patent  (10) Patent No.: US 7,695,850 B2
Sotomura et al.  (45) Date of Patent: Apr. 13, 2010

(54) ELECTRODE FOR USE IN OXYGEN REDUCTION

(75) Inventors: Tadashi Sotomura, Osaka (JP); Mitsuru Hashimoto, Osaka (JP); Yuka Yamada, Osaka (JP)

(73) Assignee: Panasonic Corporation, Osaka (JP)

( * ) Notice: Subject to any disclaimer, the term of this patent is extended or adjusted under 35 U.S.C. 154(b) by 281 days.

(21) Appl. No.: 11/808,811

(22) Filed: Jun. 13, 2007

(65) Prior Publication Data

US 2007/0243449 A1    Oct. 18, 2007

Related U.S. Application Data

(63) Continuation of application No. PCT/JP2006/316773, filed on Aug. 25, 2006.

(30) Foreign Application Priority Data

Aug. 25, 2005    (JP)    ............................. 2005-243846

(51) Int. Cl.
    *H01M 4/90*    (2006.01)
(52) U.S. Cl. ............................. 429/43; 429/42; 502/200
(58) Field of Classification Search ........................ None
    See application file for complete search history.

(56) References Cited

U.S. PATENT DOCUMENTS 5,151,515 A * 9/1992 Cisar ............................ 546/12
2003/0091889 A1* 5/2003 Sotomura et al. ............. 429/40

FOREIGN PATENT DOCUMENTS

JP    57-208073    12/1982

(Continued)

OTHER PUBLICATIONS

International Search Report, issued in corresponding International Patent Application No. PCT/JP2006/316773, dated on Nov. 7, 2006.
Lipkowski et al., "Electrocatalysis", Wiley-VCH, 1998, pp. 204-205.
Lipkowski et al., "Electrocatalysis", Wiley-VCH, 1998, pp. 232-234.

(Continued)

*Primary Examiner*—Jonathan Crepeau
*Assistant Examiner*—Tony Chuo
(74) *Attorney, Agent, or Firm*—McDermott Will & Emery LLP

(57) ABSTRACT

The present invention is usable in oxygen electrodes and air electrodes for air cells, fuel cells, electrochemical sensors and like electrochemical devices. The present invention provides a very stable oxygen-reducing electrode that can achieve electrochemical reduction of oxygen at a noble potential. The oxygen-reducing electrode of the present invention contains a cobalt tetrapyrazinoporphyrazine derivative represented by the following Structural Formula (1) as a catalytic component

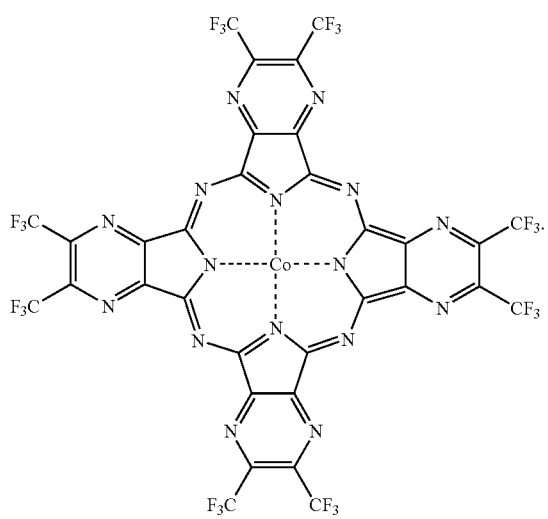

10 Claims, 5 Drawing Sheets

FOREIGN PATENT DOCUMENTS

| | | | |
|---|---|---|---|
| JP | 57-208074 | | 12/1982 |
| JP | 58-046580 | | 3/1983 |
| JP | 58-053159 | | 3/1983 |
| JP | 02-232267 | | 9/1990 |
| JP | 02-232268 | | 9/1990 |
| JP | 02-289576 | | 11/1990 |
| JP | 02-289577 | | 11/1990 |
| JP | 04-124188 | * | 4/1992 |
| JP | 11-065142 | | 3/1999 |
| JP | 11-253811 | | 9/1999 |
| JP | 2003-151567 | | 5/2003 |

OTHER PUBLICATIONS

Arihara et al., "electrocatalytic Reduction of Oxygen in a Novel Catalytic System with Cobalt Phthalocyanines and Manganese Oxide", Journal of Electrochemical Society, vol. 15, 2004, pp. A2047-A2052.

Yasuhiro Kamitori, "3-(Dimethylhydrazono)-1, 1,1,1,4,4,4-hexafluoro-2-butanone as latent perfluorobiacetyl", Tetrahedron Letters, vol. 41, pp. 9267-9270.

* cited by examiner 7A　　　7B　　　7C　　　7D

ELECTRODE FOR USE IN OXYGEN REDUCTION

This application is a continuation of International Application No. PCT/JP2006/316773, whose international filing date is Aug. 25, 2006 which in turn claims the benefit of Japanese Patent Application No. 2005-243846, filed on Aug. 25, 2005, the disclosures of which Applications are incorporated by reference herein. The benefit of the filing and priority dates of the International and Japanese Applications is respectfully requested.

TECHNICAL FIELD

The present invention relates to an oxygen-reducing electrode that uses oxygen as a material for electrode reaction.

Oxygen-reducing electrodes are used as oxygen-reducing electrodes (air electrodes) for use in electrochemical devices. Examples of electrochemical devices include zinc-air cells, aluminum-air cells, magnesium-air cells, sugar-air cells and like air cells; oxygen hydrogen fuel cells, direct methanol fuel cells and like fuel cells; and enzyme sensors, oxygen sensors and like electrochemical sensors.

BACKGROUND OF THE INVENTION

When oxygen ($O_2$) is electrolytically reduced, in the case of one-electron reduction, superoxide ($.O^{2-}$) is generated, in the case of two-electron reduction, hydrogen peroxide is generated, and in the case of four-electron reduction, water is generated (Non-Patent Document 1).

In an electrochemical device wherein an oxygen reduction reaction is a positive-electrode reaction, in order to obtain a high capacity, high voltage, and high power, it is necessary to promote such reduction reaction at a noble (plus) potential while preventing overvoltage. In other words, it is preferable that a material that can promote a four-electron reduction reaction at a high potential while preventing occurrence of overvoltage be used as the catalyst component for the positive electrode (oxygen-reducing electrode). The following documents report such catalysts.

Patent Documents 1 and 2 disclose catalysts formed of a porous molded article formed of a fluoride resin and conductive powder carrying iron phthalocyanines, cobalt porphyrins and like metal chelate compounds having oxygen-reducing abilities. These documents also disclose that, when a dimer (binuclear complex) of a metal chelate compound is used, high oxygen-reducing ability (four-electron reduction ability) can be expected, and therefore a high-power air cell can be obtained.

Non-Patent Document 2 discloses oxygen-reducing catalysts using a macrocyclic complex (e.g., a cobalt porphyrin binuclear complex) containing Cr, Mn, Fe, Co and like transition metals as center metals.

Patent Document 3 discloses an oxygen-reducing manganese complex. This complex catalyzes a four-electron oxygen reduction reaction with high selectivity. Patent Document 3 also discloses that the manganese atom has a valency of 2 to 7 and catalyzes oxygen reduction reaction in the potential range of from −0.5 V to +2 V.

However, the metal complexes disclosed in these documents have the following drawback. These metal complexes oxidize and deteriorate constituent components of cells and/or sensors, such as electrolytes, electrode reeds, current collectors, cell cases, separators, gas selective transmission membranes, etc.

Patent Document 4 discloses an oxygen-reducing complex electrode as a technique for overcoming the above drawback. This oxygen-reducing complex electrode apparently achieves four-electron reduction reaction with selectivity of almost 100%, despite this oxygen-reducing complex electrode not containing a highly oxidative catalytic component such as a metal complex containing a high valency center metal, etc.

Specifically, this oxygen-reducing complex electrode comprises Catalyst A which catalyzes a two-electron oxygen reduction reaction and Catalyst B which decomposes hydrogen peroxide formed by the two-electron oxygen reduction reaction into oxygen and water.

Metal phthalocyanines such as iron phthalocyanines, cobalt phthalocyanines, copper phthalocyanines, manganese phthalocyanines, and zinc phthalocyanines can be used as Catalyst A. Patent Document 4 discloses the following four cobalt phthalocyanine compounds.

Cobalt 4,4',4'',4'''-tetraaminophthalocyanine (abbreviated as CoTAPc) represented by Structural Formula (a) below and polymers thereof;

Cobalt hexadecafluorophthalocyanine (abbreviated as CoHFPc) represented by Structural Formula (b) below;

Cobalt tetracarboxyphthalocyanine (abbreviated as CoCOOHPc) represented by Structural Formula (c) below; and Cobalt octabutoxyphthalocyanine (abbreviated as CoOBuPc) represented by Structural Formula (d) below.

Non-Patent Document 3 discloses cobalt octacyanophthalocyanine (abbreviated as $CoPc(CN)_8$) represented by Structural Formula (e) below as a cobalt phthalocyanine compound that functions the same as Catalyst A does.

Patent Document 5, and Non-Patent Document 4 also relate to the present invention.

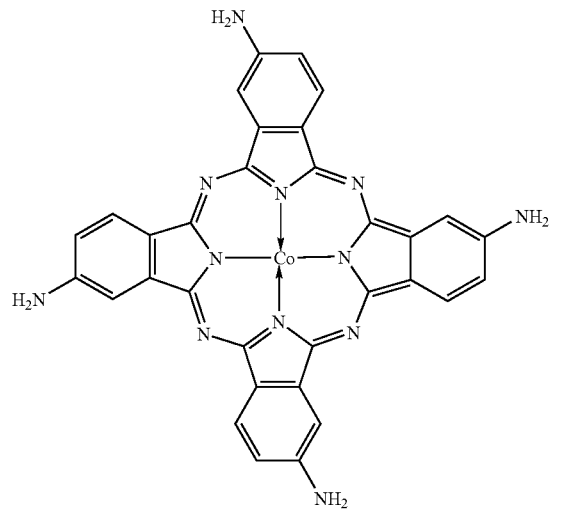

(a)

-continued (b)

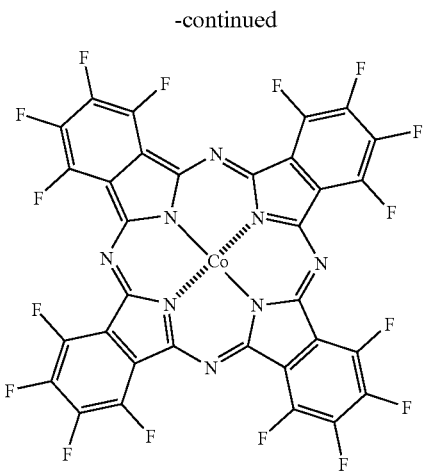

(c)

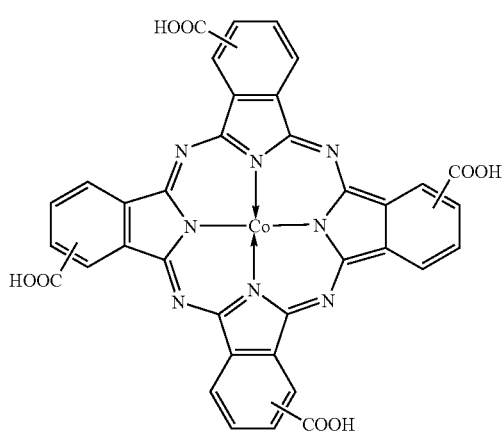

(d)

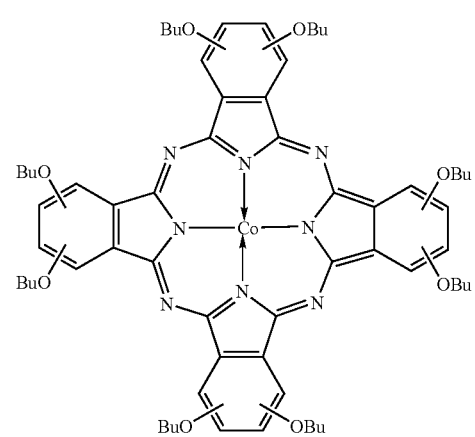

(e)

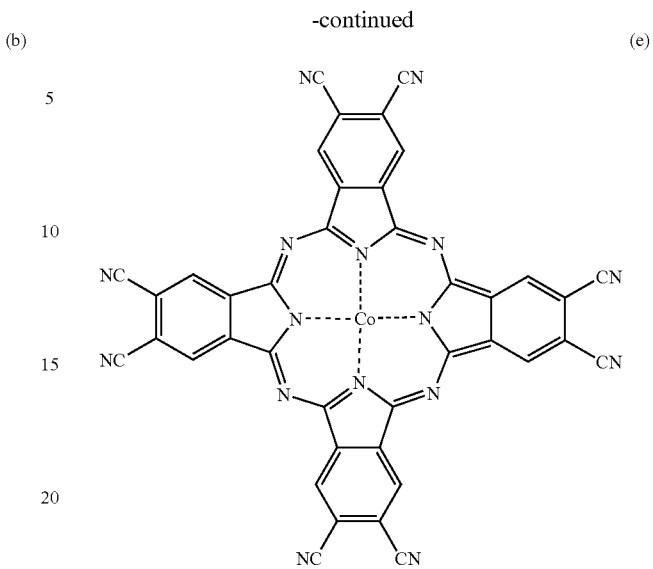

[Patent Document 1] Japanese Examined Patent Publication No. 1990-030141

[Patent Document 2] Japanese Examined Patent Publication No. 1990-030142

[Patent Document 3] Japanese Unexamined Patent Publication No. 1999-253811

[Patent Document 4] Japanese Unexamined Patent Publication No. 2003-151567

[Patent Document 5] Japanese Unexamined Patent Publication No. 1999-65142

[Non-Patent Document 1] Edited by Jacek Kipkowski and Philip N. Ross, *Electrocatalysis*, Wiley-Vch, (1998): 204-205

[Non-Patent Document 2] Edited by Jacek Kipkowski and Philip N. Ross, *Electrocatalysis*, Wiley-Vch, (1998): 232-234

[Non-Patent Document 3] Journal of Electrochemical Society, Vol. 15, 2004: A2047-A2052

[Non-Patent Document 4] Tetrahedron Letters, Vol. 41, 2000: 9267-9270

DISCLOSURE OF THE INVENTION

Problem to be Solved by the Invention

Cobalt phthalocyanine is a stable oxygen-reducing catalyst. It is known that cobalt phthalocyanine can obtain excellent oxygen-reducing characteristics without using a high valency metal element.

However, compared with cobalt phthalocyanines, platinum catalysts have greater oxygen reduction potentials. Among cobalt phthalocyanines, $CoPc(CN)_8$ and CoOBuPc have excellent oxygen reduction potentials, but are still smaller than that of platinum by 0.1 to 0.15 V.

There is a demand for chemically stable oxygen-reducing catalysts by which an oxygen-reducing electrode exhibiting as high an oxygen reduction potential as that of platinum catalysts. Platinum achieves high performance in this respect, but platinum deposits are limited and therefore cannot meet the demand on an industrial scale.

The present invention has been accomplished to overcome the above problem. In other words, an object of the present invention is to provide an oxygen-reducing electrode that uses a high-performance oxygen-reducing catalyst which can attain as high an oxygen reduction potential as that of a platinum catalyst.

Means for Solving the Problem

The present inventors conducted extensive research and found that the above object can be achieved by using a specific cobalt tetrapyrazinoporphyrazine derivative as an oxygen-reducing catalyst, and thus completed the present invention.

The present invention relates to the following oxygen-reducing electrodes and cells using the same.

1. An oxygen-reducing electrode using a cobalt tetrapyrazinoporphyrazine derivative represented by the following Structural Formula (1) as a catalytic component.

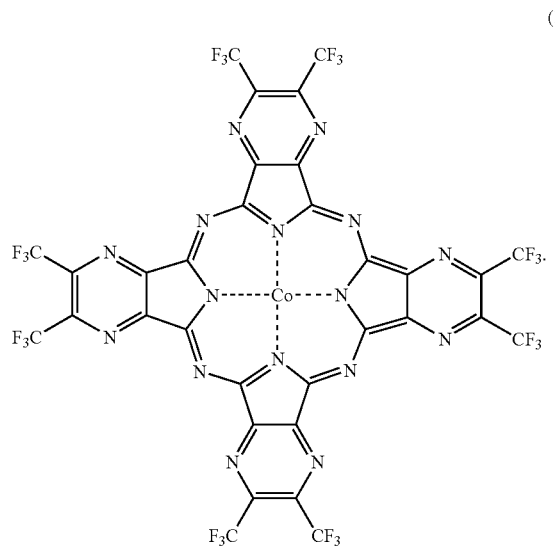

(1)

2. An oxygen-reducing electrode according to Item 1, wherein the derivative is supported on a conductive substrate.

3. An oxygen-reducing electrode according to Item 2, wherein the conductive substrate is at least one member selected from the group consisting of carbon fibers, carbon papers, carbon felts, carbon sponges, carbon nanotubes, and gold nanoparticles.

4. An oxygen-reducing electrode according to Item 1, which further comprises a hydrogen peroxide-decomposing catalyst as a catalytic component.

5. An oxygen-reducing electrode according to Item 4, wherein the hydrogen peroxide-decomposing catalyst is at least one member selected from the group consisting of manganese oxides, catalases, activated carbons, and lanthanum strontium manganese perovskite oxides.

6. An oxygen-reducing electrode according to Item 1, wherein the oxygen reduction potential is in the vicinity of $-0.2$ V in a cyclic voltammogram obtained by cyclic voltammetry, the cyclic voltammetry using a three electrode cell in which the oxygen-reducing electrode is used as the working electrode, platinum is used as the counter electrode, silver/silver chloride is used as the reference electrode, and an aqueous 0.1 mol/l potassium hydroxide solution at pH 13 is used as the electrolyte.

7. An oxygen-reducing electrode according to Item 1, wherein the oxygen reduction potential is within the range of not less than $-0.22$ V and not more than $-0.18$ V in a cyclic voltammogram obtained by cyclic voltammetry, the cyclic voltammetry using a three electrode cell in which the oxygen-reducing electrode is used as the working electrode, platinum is used as the counter electrode, silver/silver chloride is used as the reference electrode, and an aqueous 0.1 mol/l potassium hydroxide solution at pH 13 is used as the electrolyte.

8. A fuel cell using a positive electrode utilizing an oxygen reduction reaction in air as a positive electrode reaction, a negative electrode utilizing an oxidation reaction of a fuel material as a negative electrode reaction, and an electrolyte, which uses the oxygen-reducing electrode of Item 1 as the positive electrode.

9. A metal-air cell using a positive electrode utilizing an oxygen reduction reaction in air as a positive electrode reaction, a negative electrode utilizing an oxidation reaction of metal as a negative electrode reaction, and an electrolyte, which uses the oxygen-reducing electrode of Item 1 as the positive electrode.

10. A sugar-air cell using a positive electrode utilizing an oxygen reduction reaction in air as a positive electrode reaction, a negative electrode utilizing an oxidation reaction of sugar as a negative electrode reaction, and an electrolyte, which uses the oxygen-reducing electrode of Item 1 as the positive electrode.

EFFECTS OF THE INVENTION

Because the oxygen-reducing electrode of the present invention uses derivative: $CoPyrz(CF_3)_8$ represented by Structural Formula (1) as an oxygen-reducing catalyst, an oxygen reduction potential at the same level as that of platinum can be obtained. This oxygen-reducing electrode can be suitably used as an oxygen-reducing electrode (air electrode) in an air cell, fuel cell, electrochemical sensor and like electrochemical devices. Furthermore, because cobalt does not exhibit a high valence (monovalence or bivalence), deterioration due to oxidation of constituent components of an electrochemical device (e.g., electrolyte, electrodereed, current collector, etc.) can be prevented.

BRIEF DESCRIPTION OF THE DRAWINGS

FIG. 7 is a schematic diagram showing the structure of an oxygen-reducing electrode, wherein FIG. 7A shows the structure of the Example electrodes and the Comparative Example electrodes in Example 1; FIG. 7B shows the structure of the Example electrodes and the Comparative Example electrodes in Example 2; FIG. 7C shows the structure of the Example electrodes and Comparative Example electrodes in Example 3; and FIG. 7D shows the structure of the Example electrodes and Comparative Example electrodes of Examples 1, 2, and 4.

EXPLANATION OF SYMBOLS

Figure 1:
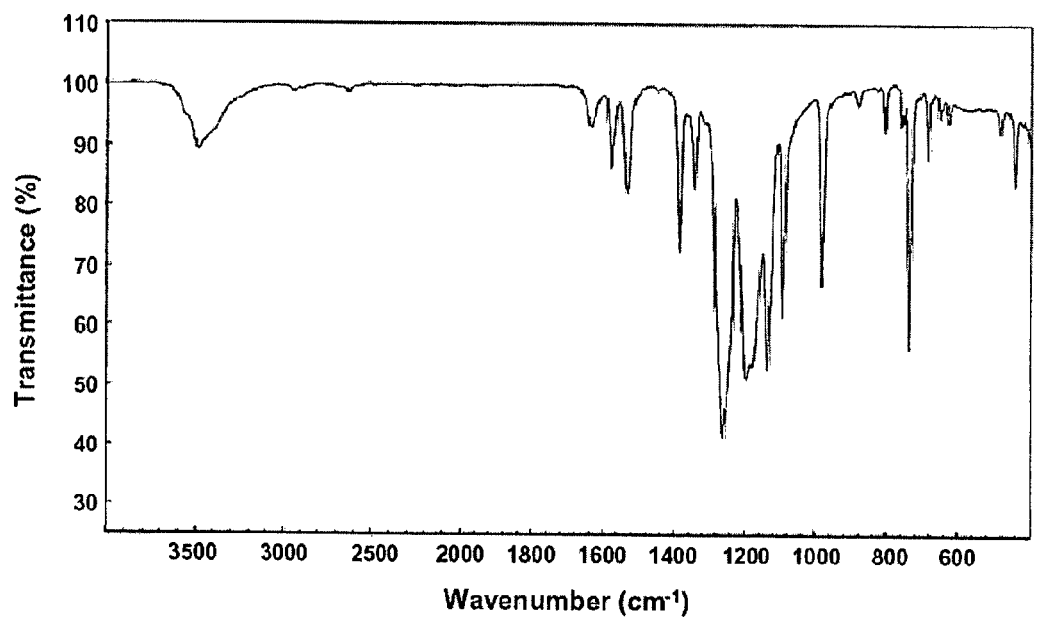
FIG. 1 is a diagram showing the infrared absorption spectrum of $CoPyrz(CF_3)_8$.

1 Carbon fiber (CFibre)
2 Gold nanoparticles (AuNano)
3 Carbon nanotube (CNT)
4 Glassy carbon (GC) pellet or gold (Au) pellet
5 Oxygen-reducing catalyst
6 Polyimide resin sheathing
7 Electrode lead wire
8 Nafion membrane containing $MnO_x$
9 Nafion membrane containing oxygen-reducing catalyst
10 Structure supporting oxygen-reducing catalyst (an oxygen-reducing catalyst is supported on a conductive substrate)
11 Fluoride resin guide ring
90 Phosphoric acid buffer
91 Fuel electrode holder
92 Glucose-oxidizing fuel electrode
93 Gold net
94 Air electrode
95 Air electrode holder
96 Gold net
97 Needle for injection
98 Needle for ejection
99 Seal ring

BEST MODE FOR CARRYING OUT THE INVENTION

The oxygen-reducing electrode of the present invention contains, as a catalytic component, a cobalt tetrapyrazinoporphyrazine derivative represented by the Structural Formula (1) below (hereunder, this cobalt tetrapyrazinoporphyrazine derivative may be referred to as the derivative of the present invention).

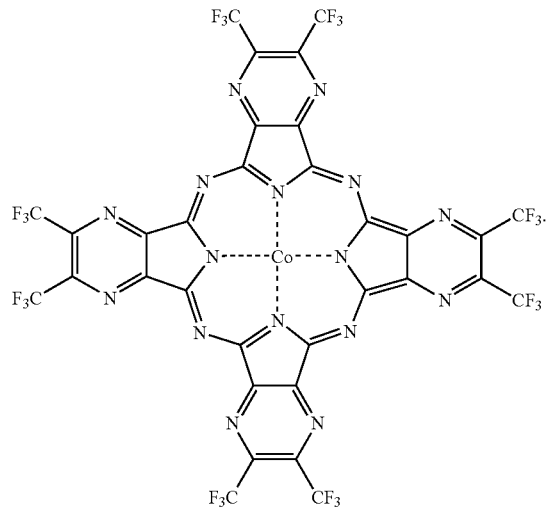

(1)

The derivative of the present invention is expressed as below.

English name: Octakis(trifluoromethyl) tetrapyrazinoporphyrazine cobalt
Abbreviation: $CoPyrz(CF_3)_8$ By containing $CoPyrz(CF_3)_8$ as an oxygen-reducing catalyst, the oxygen-reducing electrode of the present invention can attain as high an oxygen reduction potential as that of platinum. $CoPyrz(CF_3)_8$ is very stable and sublimates at 300° C. without decomposition.

A method for synthesizing the derivative of the present invention is first explained below.

(Method for Synthesizing the Derivative of the Present Invention)

The derivative of the present invention can be synthesized by a general method for synthesizing phthalocyanine derivatives. The derivative of the present invention can be synthesized by, for example, cyclizing 2,3-bis(trifluoromethyl)-5,6-dicyanopyrazine represented by Structural Formula (2) below in the presence of a cobalt compound (cobalt acetate, cobalt chloride, etc.) (Synthetic method 1).

It is also possible to synthesize the derivative of the present invention by introducing a dicyano compound to bis(trifluoromethyl)diiminoisoindoline represented by Structural Formula (3) below, and then subjecting the resultant to deammoniation in the presence of a cobalt compound (Synthetic method 2).

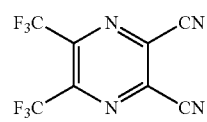

(2)

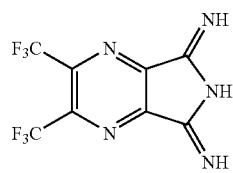

(3)

The following three methods are known as standard methods for synthesizing metal phthalocyanines:

(i) a method wherein phthalonitrile or a derivative thereof is reacted with a metal (or a metal salt);

(ii) a method wherein phthalic anhydride or phthalimide is heated together with urea and a metal (or a metal salt); and (iii) a method wherein 1,3-diiminoisoindoline is heated together with a metal (or a metal salt).

When such a method is employed to synthesize the derivative of the present invention, instead of a phthalonitrile or phthalic acid, the corresponding pyrazine derivative may be used. For example, the derivative of the present invention can be synthesized by using a 2,3-dicyano pyrazine derivative instead of phthalonitrile in the above-described method (i). This method corresponds to Synthetic method 1 described earlier. Synthetic method 1 is preferable, because the materials can be obtained easily and its production process is simple.

Synthetic method 1 can be implemented with or without solvent. There are no limitations on such solvents, and examples thereof include toluene, xylene, mesitylene, durene, chlorobenzene, dichlorobenzene, nitrobenzene, tetralin, methylnaphthalene and like aromatic hydrocarbons; pyridine, quinoline, isoquinoline and like heterocyclic compounds; dimethylaminoethanol, diethylaminoethanol and like amine compounds; dimethylformamide; dimethylacetamide; dimethylsulfoxide; methylpyrrolidone; etc.

When this method is implemented without solvent, it is preferable that anhydrous sodium sulfate, anhydrous magnesium sulfate, calcium chloride or a like mineral salt coexist in the reaction system. In the presence of a mineral salt, overheating due to reaction heat can be reduced.

It is preferable that the reaction temperature be in the range of from 100 to 250° C. The reaction barely proceeds at low temperatures, but side reactions, such as partial decomposition, may occur at high temperatures. The reaction time can be suitably selected depending on the reaction temperature, but is generally 5 minutes to several hours. It is preferable that the reaction atmosphere be an inert gas, nitrogen or like non-oxidizing atmosphere, but air may be used.

The proportion of the dicyano pyrazine derivative to the cobalt compound represented by Structural Formula (2) may be selected so that one cobalt atom is contained per four molecules of the derivative (theoretical amount), but, if necessary, one of these may be used in excess up to several times the theoretical amount. For example, such a proportion can be suitably selected depending on the yield, operability, target purity, etc.

Purification of the reaction product (derivative of the present invention) can be conducted by washing with water and/or various other solvents, recrystallization, sublimation, column chromatography, liquid chromatography, etc. Such purification methods may be employed in a combined manner.

The dicyano pyrazine derivative represented by Structural Formula (2) may be synthesized in-house or be a commercially available product. When synthesized in-house, the method disclosed in Non-Patent Document 4 can be employed. In this method, trifluoroacetoaldehyde N,N-dimethylhydrazone is synthesized by reacting 1-ethoxy-2,2,2-trifluoroethanol with N,N-dimethylhydrazine. An anhydrous trifluoroacetate is then reacted with the hydrazone in chloroform in the presence of dimethylethylamine. The hydrazone is thus trifluoroacetylated. A dicyanopyrazine derivative is synthesized by reacting the resultant trifluoroacetylated hydrazone with 1,2-diamino-1,2-dicyanoethylene without conducting isolation.

Cobalt compounds (including cobalt metal and cobalt salts) are explained below. Commercially available cobalt compounds may be used. There are various forms of such cobalt compounds including wires, sponges, powders, etc., but a powder of as small particle as possible is preferable to smoothly promote the reaction. Examples of cobalt salts include cobalt chloride, cobalt bromide, cobalt sulfate, cobalt nitrate, cobalt formate, cobalt acetate, cobalt benzoate, etc. Any types of salts can be used regardless of whether they are anhydrous or hydrated salts.

(The Oxygen-Reducing Electrode of the Present Invention)

The oxygen-reducing electrode of the present invention contains $CoPyrz(CF_3)_8$ as a catalytic component. Such an oxygen-reducing electrode may have the same structure as that of known oxygen-reducing electrodes except for CoPyrz $(CF_3)_8$ being contained as a catalytic component.

There are no limitations on how the oxygen-reducing electrode contains $CoPyrz(CF_3)_8$, and $CoPyrz(CF_3)_8$ can be handled in the same manner as conventional oxygen-reducing catalysts. For example, it is possible to support $CoPyrz(CF_3)_8$ directly on a glassy carbon (GC) electrode or gold (Au) electrode. It is also possible to support $CoPyrz(CF_3)_8$ on a separately prepared carrier (conductive substrate) and then dispose the carrier so as to be in contact with a GC electrode or an Au electrode.

When a carrier is separately prepared, it is preferable that a conductive substrate having a large specific surface area be used as a carrier, because externally supplied electrons can be effectively delivered to oxygen molecules. By increasing the efficiency of electron transfer, overvoltage can be prevented and the oxygen reduction reaction can smoothly proceed.

Examples of preferable conductive substrates include carbon fibers (CFibre), carbon papers (CP), carbon felts (CF), carbon sponges (CSponge), carbon nanotubes (CNT), gold nanoparticles (AuNano), etc. Such conductive substrates may be used in a combined manner.

The above-exemplified conductive substrates are preferable because they have high conductivities and large specific surface areas. By using such a conductive substrate, the contact area between the oxygen-reducing catalyst, oxygen molecules, and electrolyte is increased and performance of the electrode can be improved.

Figure 3:
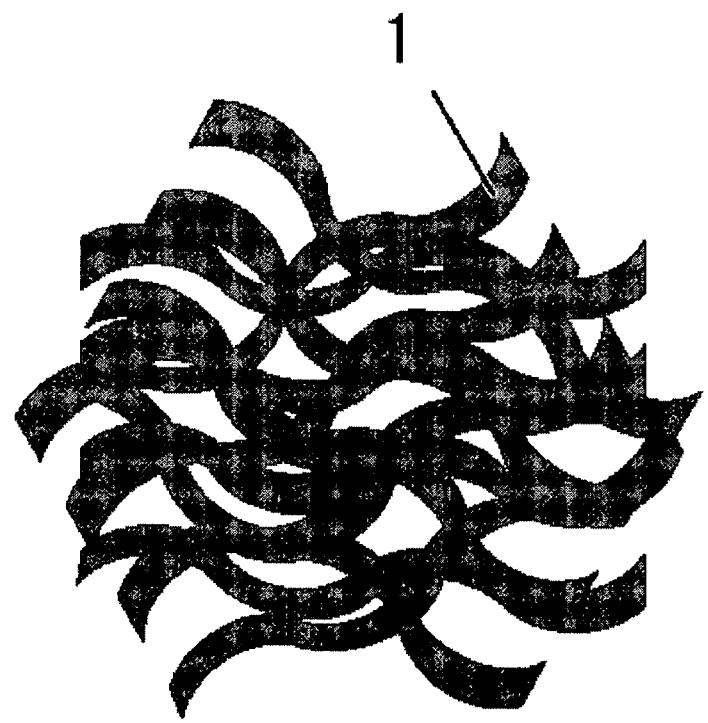
FIG. 3 is a schematic diagram showing the structure of a conductive substrate (carbon felt (CF)).

The CF mentioned above can be obtained by making CFibres having a cross-sectional diameter of several μm randomly entwine with each other. It is also possible to obtain such a CF by carbonating a felt formed of artificial fibers or natural fibers. FIG. 3 shows a schematic diagram of a CF. In FIG. 3, numerical symbol 1 indicates a CFibre.

Figure 4:
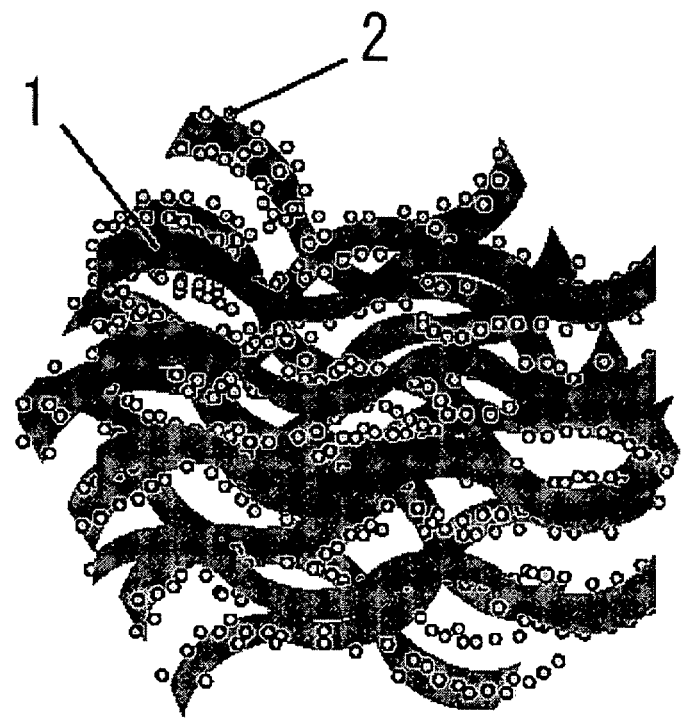
FIG. 4 is a schematic diagram showing the structure of a conductive substrate (CF-AuNano) comprising carbon felt (CF) and gold nanoparticles (AuNano).

FIG. 4 shows a schematic diagram of a conductive substrate (CF-AuNano) formed by combining CF with AuNano. In FIG. 4, numerical symbol 1 indicates a CFibre, and numerical symbol 2 indicates an AuNano.

The CF-AuNano mentioned above can be obtained by impregnating a CF with a dispersion of AuNano, and then removing the dispersion medium. An example of CF-AuNano preparation is described below.

An aqueous solution obtained by dissolving 0.75 mmol of chloroauric acid ($HAuCl_4$) in 25 ml of water is added to a toluene solution obtained by dissolving 1.5 g of tetraoctylammonium bromide in 80 ml of toluene, followed by stirring. The organic phase is then isolated.

Decanethiol (360 μl) is added to the resultant organic phase, and a solution obtained by dissolving 0.77 g of sodium borohydride ($NaBH_4$), which is a reducing agent, in 25 ml of water is gradually added to the organic phase drop by drop. This precipitates AuNano having a diameter of about 2 nm. Here, the decanethiol serves as a capping agent and makes the AuNano particles' size uniform. The AuNano diameter can be controlled within the range of several nm to several dozen nm by changing the type of reducing agent and/or capping agent. For example, when sodium citrate is used instead of the decanethiol in the above example, AuNano having a diameter of about 18 nm can be obtained.

The resultant AuNano is washed with ethanol and then dispersed in hexane, giving a hexane dispersion. In the hexane dispersion, the AuNano surface is covered with a decanethiol monomolecular film, and the AuNano is uniformly dispersed in the dispersion.

After impregnating a CF with the hexane dispersion, the hexane is evaporated. The decanethiol is then decomposed and removed by heating at about 300° C., obtaining CF-AuNano.

It is also possible to clean the surface of the CF-AuNano, if necessary, by dipping the CF-AuNano in a piranha solution (a solution obtained by mixing 4 parts by weight of concentrated sulfuric acid and 1 part by weight of hydrogen peroxide).

Figure 5:
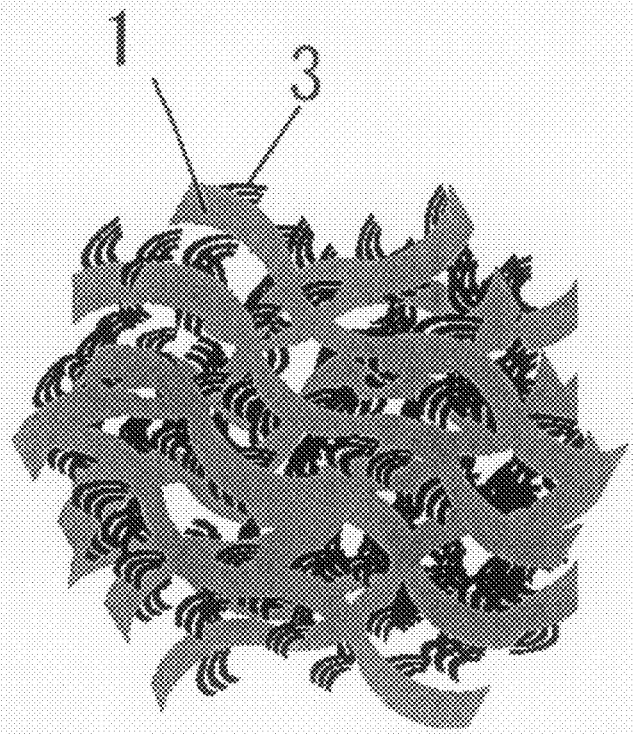
FIG. 5 is a schematic diagram showing the structure of a conductive substrate (CF-CNT) comprising carbon felt (CF) and carbon nanotubes (CNT).

FIG. 5 shows a schematic diagram of a conductive substrate (CF-CNT) obtained by combining a CF with CNT. In FIG. 5, numerical symbol 1 is a CFibre, and numerical symbol 3 is a CNT.

The above-explained CF-CNT can be obtained by, for example, impregnating a CF with a CNT dispersion, and then removing the dispersion medium. Dimethylformamide (DMF) is preferably used as the dispersion medium. A method for preparing a CF-CNT is explained below.

First, 100 mg of single-wall carbon nanotubes (diameter of about 1.1 nm, length of 0.5 to 100 μm, abbreviated as SWCNT) is dipped in a piranha solution, and heated at 80° C. for 4 to 5 hours. The resultant solution is subjected to filtration, and the solid components are neutralized by washing with a saturated sodium bicarbonate solution, and then vacuum dried.

Second, DMF is added to the dried SWCNT powder in a proportion of 1 ml of DMF per 10 mg of dried SWCNT powder, and then the mixture is subjected to ultrasonic mixing and dispersion, giving a dispersion containing SWCNT powder dispersed in DMF. A CF is impregnated with the DMF dispersion solution, and the DMF is then evaporated, giving CF-CNT.

Examples of CNT include the above-mentioned SWCNT, multi-wall carbon nanotubes (diameter of about 70 nm, length of 0.5 to 500 μm, abbreviated as MWCNT), and double-wall carbon nanotubes (diameter of about 3 nm, length of 0.5 to 150 μm, abbreviated as DWCNT).

In the above-described preparative examples, impregnation in a piranha solution followed by heating increases the number of COOH groups on the surface of the CNT. This enhances chemisorption on the surface of the CNT. In other words, if increase in chemisorptivity of the surface of the CNT is unnecessary, impregnation and heating can be omitted.

Figure 6:
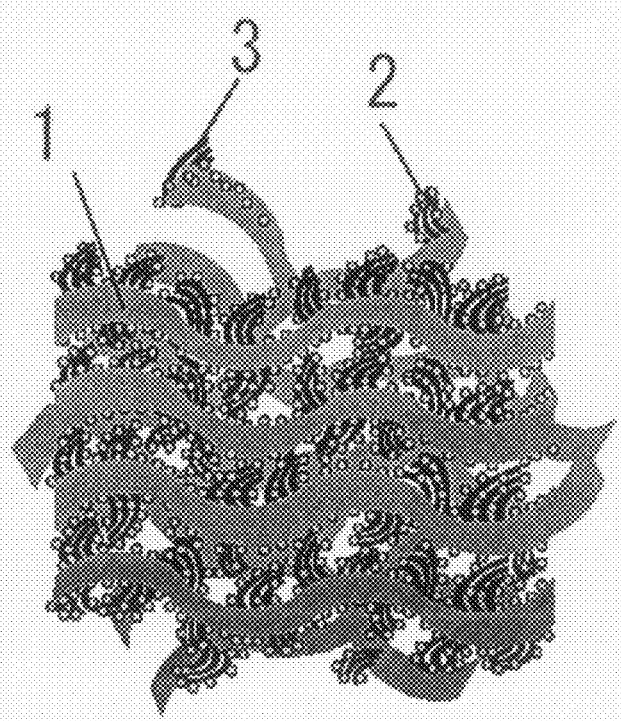
FIG. 6 is a schematic diagram showing the structure of a conductive substrate (CF-CNT-AuNano) comprising carbon felt (CF), carbon nanotubes (CNT) and gold nanoparticles (AuNano).

FIG. 6 shows a schematic diagram of a conductive substrate (CF-CNT-AuNano) obtained by combining CF, CNT with AuNano. In FIG. 6, numerical symbol 1 is CFibre, numerical symbol 2 is AuNano, and numerical symbol 3 is CNT.

The above CF-CNT-AuNano can be obtained by, for example, impregnating a CF-CNT with an Au-Nano dispersion, and then removing the dispersion medium. The above-described hexane dispersion is an example of an Au-Nano dispersion. Methods for preparing and impregnating the hexane dispersion, removal of the dispersion medium, and preparation of CF-CNT may be the same as described above.

Examples of the methods for supporting the derivative of the present invention (CoPyrz(CF$_3$)$_8$) on a carrier (CG electrode, Au electrode, the above-described conductive substrate, etc.) include vacuum deposition and like dry processes, and solution impregnation and like wet processes.

Because CoPyrz(CF$_3$)$_8$ has a higher solubility in various solvents than the cobalt phthalocyanine compounds represented by Structural Formulae (a) to (e), a uniform solution with a low concentration of about 0.01 wt % to a high concentration of about several tens wt % can be easily obtained. Therefore, supporting can be easily conducted by a wet process.

Examples of solvents usable in wet processing include ethanol, propanol, acetone, methyl ethyl ketone, acetonitrile, dimethylformamide (DMF), dimethyl sulfoxide (DMSO) and like protic and aprotic polar organic solvents; and hexane, tetrahydrofuran (THF), ethyl acetate and like nonpolar organic solvents.

The oxygen-reducing electrode of the present invention may contain CoPyrz(CF$_3$)$_8$ together with other catalytic components. The oxygen-reducing electrode of the present invention may further contain, for example, Catalytic component A that generates hydrogen peroxide and/or superoxide by oxygen reduction, and a Catalytic component B that decomposes hydrogen peroxide and/or superoxide into oxygen and water. In the above-described examples, when the oxygen-reducing electrode of the present invention additionally contains a hydrogen peroxide decomposing catalyst, a large oxygen reduction current can be attained because the oxygen-reducing electrode can conduct four-electron oxygen reduction as the same as platinum, and therefore preferable. The oxygen-reducing electrode of the present invention may further contain known conductive materials and/or ion conductors. In this case, electrical resistance and overvoltage of the oxygen-reducing electrode can be easily reduced.

Examples of materials usable for Catalytic component A include platinum, cobalt, ruthenium, palladium, nickel, gold, silver, copper, platinum-cobalt alloys, platinum-ruthenium alloys and like metal materials; graphite, activated carbon and like carbon materials; copper oxide, nickel oxide, cobalt oxide, ruthenium oxide, lead oxide, molybdenum oxide, manganese dioxide, lead ruthenate, lanthanum-manganese-copper perovskite oxides and like metal oxides; iron phthalocyanines, cobalt phthalocyanines, copper phthalocyanines, manganese phthalocyanines, zinc phthalocyanines and like metal phthalocyanines having a porphyrin ring; and metal porphyrins, ruthenium ammine complexes, cobalt ammine complexes, cobalt ethylene diamine complexes and like metal complexes.

It is preferable that the material for Catalytic component B be at least one member selected from the group consisting of catalases, glutathione peroxidase and like hydrogen peroxide decomposing enzymes; metal oxides (in particular, manganese oxide), activated carbons (in particular, brewer's yeast-activated carbon, Bincho carbon (activated carbons obtained by heating oak, Japanese oak and like woody materials)); and lanthanum strontium manganese perovskite oxides. Among these, metal oxides having a high affinity for hydrogen peroxide and high oxygen exchange ability for capturing and releasing oxygen are particularly preferable. Examples of such metal oxides include $Mn_2O_3$, $Mn_3O_4$, $Mn_5O_8$, γ-MnOOH (a mixture of $Mn_3O_4$ and $Mn_5O_8$) and like manganese lower oxides ($MnO_x$) that can be obtained by subjecting $MnSO_4$ and like divalent manganese salts to chemical oxidation using hydrogen peroxide, etc., and, if necessary, further subjecting the resultant to heating under an oxygen-containing atmosphere. In addition to the above, platinum black, ruthenium oxide, $Cu_{x-1}Sr_xTiO_3$ (x=0 to 0.5), $La_xSr_{1-x}MnO_3$ (x=0 to 0.5), $SrTiO_3$ and like perovskite oxides are useable.

Among these, manganese lower oxides are particularly preferable because they have a high hydrogen peroxide decomposing activity, suffer from less deterioration, and are inexpensive. Manganese lower oxides are manganese oxides whose manganese atom valency is less than 4. Positive electrode materials from spent manganese cells and calcined such materials can be reused as manganese lower oxides. Therefore, manganese lower oxides are also preferable in terms of reusing and/or recycling resources.

When a catalytic component, a conductive material, and an ionic conductor are used together in an oxygen-reducing electrode, it is preferable that such components be disposed so as to be in contact one another. Such an arrangement readily decreases overvoltaging of the oxygen-reducing electrode.

There are no limitations on electrolytes usable together with the oxygen-reducing electrode, and any types of electrolytes such as alkaline, neutral, and acidic aqueous solutions; organic electrolytes; ion-conductive polymers; and ionic liquids can be used. Among these, a low concentration alkaline solution (not higher than 1 M) having a high oxygen solubility and diffusion rate is preferable because it can easily generate an oxygen reduction reaction.

The oxygen-reducing electrode of the present invention possesses the following oxygen-reducing properties.

The oxygen reduction potential is in the vicinity of −0.2 V (in particular, within the range of from −0.22 V to −0.18 V) in a cyclic voltammogram obtained by cyclic voltammetry that uses a three electrode cell in which the oxygen-reducing electrode is used as the working electrode, platinum is used as the counter electrode, silver/silver chloride (saturated KCl) is used as the reference electrode, and an aqueous 0.1 mol/l potassium hydroxide solution (pH 13) saturated with dissolved oxygen by contacting pure oxygen gas for 30 minutes is used as the electrolyte. The cyclic voltammetry method can be conducted by the following process. The potential of the working electrode relative to the reference electrode is swept from +0.4 V to −1.2 V at a sweep rate of 10 mV/s. Upon reaching −1.2 V, the potential is swept toward 0 V at a sweep rate of 10 mV/s. During the potential sweeping, the electric current applied across the working electrode and the counter electrode is recorded relative to the potential of the working electrode.

EXAMPLES

The present invention is explained in detail below with reference to Examples and Comparative Examples.

Synthetic Example 1

Synthesizing the Derivative of the Present Invention: CoPyrz(CF$_3$)$_8$ 2,3-bis(trifluoromethyl)-5,6-dicyanopyrazine (2.66 g), 0.49 g of cobalt (II) acetate and 8.0 g of anhydrous sodium sulfate were mixed.

The resultant mixture was heated from room temperature to 200° C. over 45 minutes using an oil bath. During heating, the reaction started around 120° C. and the reaction system gradually became purple. After being kept at 200° C. for 30 minutes, the mixture was cooled to room temperature.

The reaction mixture was washed with water and dried after removing anhydrous sodium sulfate and/or acetic acid, giving 2.55 g of coarse derivative of the present invention (purple black powder).

The resultant coarse derivative was purified using column chromatography (stationary phase: silica gel, mobile phase: tetrahydrofuran). The result of quantitative analysis for cobalt in the purified derivative of the present invention (purple black powder) was 5.5%, which falls within the error range from the theoretical value of 5.25%.

In the infrared absorption spectrum (KBr tablet method) of the purified derivative, a strong absorption peak attributable to CF$_3$ was observed in the vicinity of 1260 cm$^{-1}$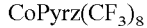. An absorption peak attributable to a substituted imine was observed in the vicinity of 1630 cm$^{-1}$ (FIG. 1).

Figure 2:
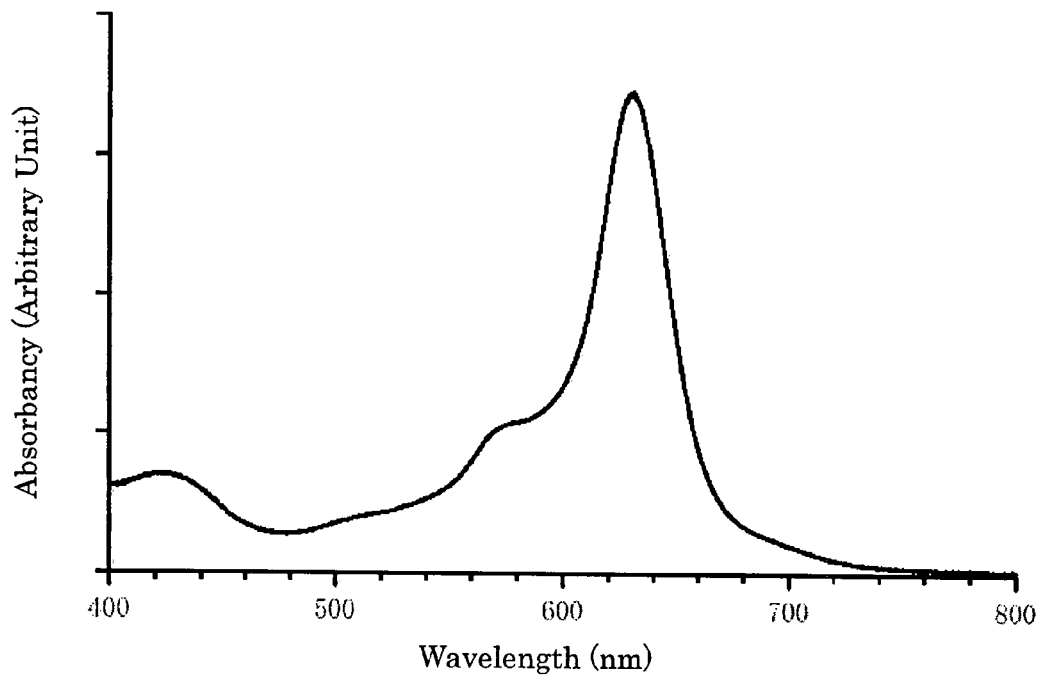
FIG. 2 is a diagram showing the electronic spectrum of $CoPyrz(CF_3)_8$.

In the electronic spectrum of the purified derivative (in acetone), a strong absorption was observed at 630 nm corresponding to the strong absorption in the vicinity of 600 to 700 nm specific to phthalocyanines (FIG. 2).

Synthesize of the derivative of the present invention was confirmed based on the above results.

Example 1

Preparation of Example Electrodes 1 to 6, and Comparative Example Electrodes 101 to 112

Figure 7:
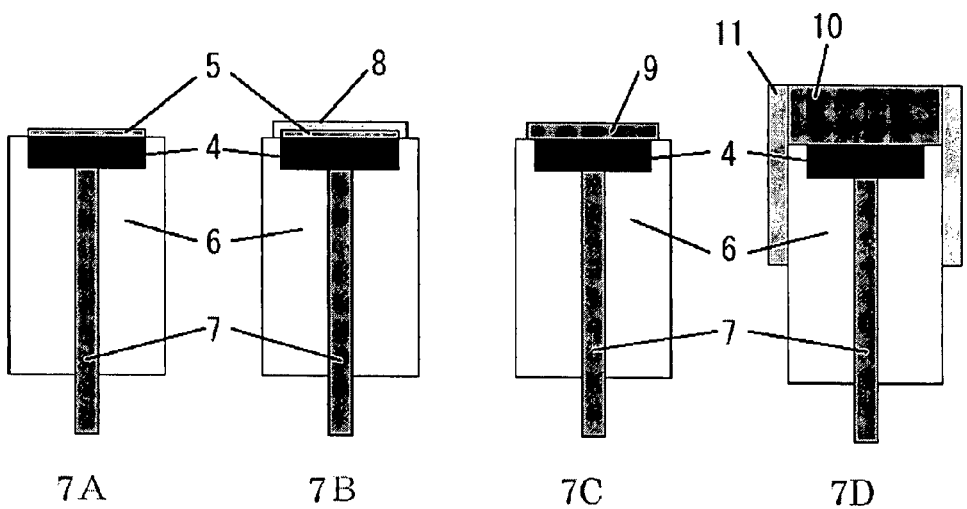

Example electrodes 1 and 4, and Comparative Example electrodes 101, 104, 107, and 110 have the cross-sectional structure shown in FIG. 7A. Numerical symbols 4, 6 and 7 in FIG. 7A are as explained below.

Numerical symbol 4 is a GC electrode or Au electrode. The GC electrode or Au electrode is a pellet having a thickness of 5 mm and diameter of 6 mm. An electrode lead wire 7 is connected to one surface of the electrode pellet, and a catalyst is supported on the other surface. The electrode pellet and the electrode lead wire are accommodated in a polyimide resin sheathing 6 having a diameter of 10 mm and a length of 80 mm. The same explanations of numerical symbols 4, 6, and 7 can also be applied to FIGS. 7B to 7D.

Numerical symbol 5 in FIG. 7A is an oxygen-reducing catalyst.

Example electrodes 2, 3, 5 and 6, and Comparative Example electrodes 102, 103, 105, 106, 108, 109, 111 and 112 have the cross-sectional structure shown in FIG. 7D.

Numerical symbol 10 in FIG. 7D is an oxygen-reducing catalyst supported on an conductive substrate. The conductive substrate is CF (sold by Tsukuba Materials Information Laboratory Ltd., product number: e-4-1, carbon felt, thickness of 2 mm), CF-CNT (product of Aldrich Corporation, multi-wall carbon nanotube), CF-AuNano (average particle diameter of 2 nm) or CF-CNT-AuNano (average particle diameter of 2 nm). Numerical symbol 11 is a fluorocarbon guide ring for maintaining the support 10 so as to electrically connect with the electrode pellet.

The catalysts and carriers (including electrode pellets) used in each oxygen-reducing electrode are shown in Table 1.

In each oxygen-reducing electrode, the catalyst was supported by a wet process. The details of the wet process are as below.

First, a 1 wt % (about 10 mM) solution was prepared by dissolving the oxygen-reducing catalyst in DMF. The solution obtained by dissolving CoPyrz(CF$_3$)$_8$ was uniform without agglomeration. However, solutions of CoPc(CN)$_8$ and CoHFPc formed gel-like agglomerates.

The carriers (the supporting surfaces of conductive substrates and electrode pellets) were dipped in an above-described solution for about 5 minutes while stirring the solution. The oxygen-reducing catalysts were supported on the carriers by subsequently conducting hot air drying, thus preparing each oxygen-reducing electrode.

(Evaluation of Oxygen-Reducing Electrode)

Oxygen-reducing properties of each electrode were evaluated using a cyclic voltammogram obtained by cyclic voltammetry that used a three electrode cell in which the oxygen-reducing electrode was used as the working electrode, platinum was used as the counter electrode, silver/silver chloride (saturated KCl) was used as the reference electrode, and an aqueous 0.1 mol/l potassium hydroxide solution at pH 13 saturated with dissolved oxygen by contacting pure oxygen gas for 30 minutes was used as the electrolyte.

Figure 8:
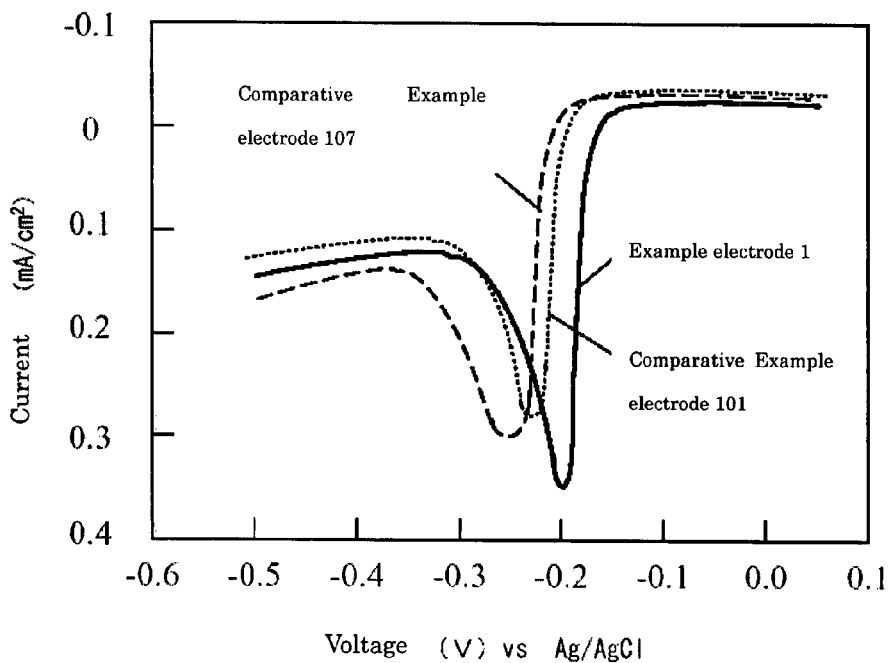
FIG. 8 is a diagram showing the current-potential properties of oxygen-reducing electrodes (Example electrode 1, and Comparative Example electrodes 101 and 107).

Specifically, the potential of the working electrode relative to the reference electrode is swept from +0.4 V to −1.2 V at a sweep rate of 10 mV/s. Upon reaching −1.2 V, the potential is swept toward 0 V at a sweep rate of 10 mV/s. During the potential is being swept, electric current across the working electrode and the counter electrode is recorded relative to the potential of the working electrode. FIG. 8 shows the evaluation results of Example electrode 1, Comparative Example electrode 101, and Comparative Example electrode 107.

In FIG. 8, the solid line indicates the current-potential curve of Example electrode 1, the dotted line indicates the current-potential curve of Comparative Example electrode 101, and the dashed line indicates the current-potential curve of Comparative Example electrode 107. The peak potentials (Ep) and peak currents (Ip: apparent current per unit area of electrode) of the reduction current at each oxygen reduction reaction are as follows:

Example electrode 1 Ep: −0.20 V, Ip: 0.35 mA/cm$^2$,

Comparative Example electrode 101 Ep: −0.23 V, Ip: 0.28 mA/cm$^2$,

Comparative Example electrode 107 Ep: −0.25 V, Ip: 0.30 mA/cm$^2$.

Table 1 shows the evaluation results (Ep, Ip) of Example electrodes 1 to 5, and Comparative Example electrodes 101 to 112.

TABLE 1

| Test electrode | Oxygen-reducing catalyst | Carrier | Peak potential of oxygen reduction current: Ep (Volt vs Ag/AgCl) | Current at peak potential: Ip (mA/cm$^2$) |
|---|---|---|---|---|
| Example electrode 1 | CoPyrz(CF$_3$)$_8$ | GC | −0.20 | 0.35 |
| Example electrode 2 | CoPyrz(CF$_3$)$_8$ | CF | −0.21 | 2.0 |
| Example electrode 3 | CoPyrz(CF$_3$)$_8$ | CF-CNT | −0.21 | 2.8 |
| Example electrode 4 | CoPyrz(CF$_3$)$_8$ | Au | −0.19 | 0.32 |
| Example electrode 5 | CoPyrz(CF$_3$)$_8$ | CF-AuNano | −0.19 | 3.3 |
| Example electrode 6 | CoPyrz(CF$_3$)$_8$ | CF-CNT-AuNano | −0.20 | 3.7 |
| Comp. Ex. electrode 101 | CoPc(CN)$_8$ | GC | −0.23 | 0.28 |
| Comp. Ex. electrode 102 | CoPc(CN)$_8$ | CF | −0.25 | 0.51 |
| Comp. Ex. electrode 103 | CoPc(CN)$_8$ | CF-CNT | −0.26 | 0.53 |
| Comp. Ex electrode 104 | CoPc(CN)$_8$ | Au | −0.23 | 0.25 |
| Comp. Ex. electrode 105 | CoPc(CN)$_8$ | CF-AuNano | −0.24 | 0.60 |
| Comp. Ex. electrode 106 | CoPc(CN)$_8$ | CF-CNT-AuNano | −0.23 | 0.59 |
| Comp. Ex. electrode 107 | CoHFPc | GC | −0.25 | 0.30 |
| Comp. Ex. electrode 108 | CoHFPc | CF | −0.28 | 0.54 |
| Comp. Ex. electrode 109 | CoHFPc | CF-CNT | −0.27 | 0.57 |
| Comp. Ex. electrode 110 | CoHFPc | Au | −0.25 | 0.26 |
| Comp. Ex. electrode 111 | CoHFPc | CF-AuNano | −0.27 | 0.55 |
| Comp. Ex. electrode 112 | CoHFPc | CF-CNT-AuNano | −0.28 | 0.62 |

Evaluation

Because Example electrodes 1 to 6 contain CoPyrz(CF$_3$)$_8$, they can reduce oxygen at a more noble potential than Comparative Example electrodes 101 to 112. CoPyrz(CF$_3$)$_8$ can be uniformly supported on a conductive substrate because of its high solubility in solvents. This increases the oxygen reduction activity sites, and therefore a greater reduction current can be obtained. Such effects are remarkable when a conductive substrate is used. For example, in Example electrode 2 wherein the oxygen-reducing catalyst was supported on a CF, the Ip was about six times that of Example electrode 1 wherein the oxygen-reducing catalyst was supported on a GC electrode pellet. However, in Comparative Example electrode 102 wherein the oxygen-reducing catalyst was supported on CF, only about two times the Ip could be obtained compared to Comparative Example electrode 1 wherein the oxygen-reducing catalyst was supported on a GC electrode pellet.

Example 2

Preparation of Example Electrodes 7 to 12, and Comparative Example Electrodes 113 to 124

Example electrodes 7 and 10, and Comparative Example electrodes 113, 116, 119, and 123 have the cross-sectional structure shown in FIG. 7B.

In FIG. 7B, numerical symbol 8 is a Nafion membrane containing MnO$_x$.

Example electrodes 8, 9, 11 and 12, and Comparative Example electrodes 114, 115, 117, 118, 120, 121, 123 and 124 have the cross-sectional structure shown in FIG. 7D.

In FIG. 7D, numerical symbol 10 is an oxygen-reducing catalyst supported on a conductive substrate together with MnO$_x$ and Nafion (product of Du Pont, product name: Nafion 117).

Table 2 shows the catalyst, carrier (including electrode pellet), etc., used in each oxygen-reducing electrode.

In each oxygen-reducing electrode, the catalyst was supported by a wet process. The details of the wet process are as below.

First, an oxygen-reducing catalyst was supported in the same manner as in Example 1. Second, a Nafion membrane was additionally supported by dipping the oxygen-reducing catalyst in an ethanol solution dissolving 0.05 wt % Nafion for 1 minute, followed by hot air drying for two hours. Third, using the electrode supporting a Nafion membrane as the working electrode, MnO$_x$ (manganese oxide) was deposited by electrodeposition from an aqueous solution containing 0.1 M manganese acetate and 0.1 M sodium sulphate by repeating a potential sweep between 0 V and 0.40 V 60 times using an Ag/AgCl (saturated KCl) electrode as the reference electrode and platinum as the counter electrode. An oxygen-reducing electrode was thus prepared. The amount of MnO$_x$ supported increased depending on the number of potential sweeps repeated, and was about 0.3 mg/cm$^2$ after completion of 60 potential sweeps. MnO$_x$ was deposited on the Nafion membrane in a form of particles; some were connected to others and others were dispersed.

(Evaluation of Oxygen-Reducing Properties of Electrodes)

Oxygen-reducing properties of the electrodes were evaluated in the same manner as in Example 1.

Table 2 shows the results (Ep, Ip) of Example electrodes 7 to 12, and Comparative Example electrodes 113 to 124.

TABLE 2

| Test electrode | Oxygen-reducing catalyst | Hydrogen peroxide decomposing catalyst | Carrier | Ep (Volt vs Ag/AgCl) | IP (mA/cm$^2$) |
|---|---|---|---|---|---|
| Example electrode 7 | CoPyrz(CF$_3$)$_8$ | MnO$_x$ | GC | −0.21 | 0.65 |
| Example electrode 8 | CoPyrz(CF$_3$)$_8$ | MnO$_x$ | CF | −0.21 | 3.8 |
| Example electrode 9 | CoPyrz(CF$_3$)$_8$ | MnO$_x$ | CF-CNT | −0.22 | 5.4 |
| Example electrode 10 | CoPyrz(CF$_3$)$_8$ | MnO$_x$ | Au | −0.21 | 0.60 |
| Example electrode 11 | CoPyrz(CF$_3$)$_8$ | MnO$_x$ | CF-AuNano | −0.20 | 6.1 |
| Example electrode 12 | CoPyrz(CF$_3$)$_8$ | MnO$_x$ | CF-CNT-AuNano | −0.21 | 7.0 |
| Comp. Ex. electrode 113 | CoPc(CN)$_8$ | MnO$_x$ | GC | −0.25 | 0.32 |
| Comp. Ex. electrode 114 | CoPc(CN)$_8$ | MnO$_x$ | CF | −0.27 | 0.55 |
| Comp. Ex. electrode 115 | CoPc(CN)$_8$ | MnO$_x$ | CF-CNT | −0.29 | 0.55 |
| Comp. Ex. electrode 116 | CoPc(CN)$_8$ | MnO$_x$ | Au | −0.24 | 0.27 |
| Comp. Ex. electrode 117 | CoPc(CN)$_8$ | MnO$_x$ | CF-AuNano | −0.26 | 0.65 |
| Comp. Ex. electrode 118 | CoPc(CN)$_8$ | MnO$_x$ | CF-CNT-AuNano | −0.25 | 0.60 |
| Comp. Ex. electrode 119 | CoHFPc | MnO$_x$ | GC | −0.28 | 0.25 |
| Comp. Ex. electrode 120 | CoHFPc | MnO$_x$ | CF | −0.30 | 0.57 |
| Comp. Ex. electrode 121 | CoHFPc | MnO$_x$ | CF-CNT | −0.29 | 0.60 |
| Comp. Ex. electrode 122 | CoHFPc | MnO$_x$ | Au | −0.27 | 0.28 |
| Comp. Ex. electrode 123 | CoHFPc | MnO$_x$ | CF-AuNano | −0.29 | 0.56 |
| Comp. Ex. electrode 124 | CoHFPc | MnO$_x$ | CF-CNT-AuNano | −0.30 | 0.65 |

Evaluation

Because Example electrodes 7 to 12 contain CoPyrz(CF$_3$)$_8$, they can conduct oxygen reduction at a higher (more noble) potential than Comparative Example electrodes 113 to 124. CoPyrz(CF$_3$)$_8$ can be uniformly supported on a conductive substrate because of its high solubility in solvents. This increases the oxygen-reduction activity sites, and therefore a great reduction current can be attained. Such effects are remarkable when a conductive substrate is used. For example, in Example electrode 8 wherein an oxygen-reducing catalyst was supported on a CF, the IP was about six times that of Example electrode 7 wherein the oxygen-reducing catalyst was supported on a GC electrode pellet. However, in Comparative Example electrode 114 wherein the oxygen-reducing catalyst is supported on a CF, only about two times the Ip could be obtained compared to Comparative Example electrode 113 wherein the oxygen-reducing catalyst was supported on a GC electrode pellet. The same effect can be achieved even if MnO$_x$ which is a hydrogen peroxide decomposing catalyst, and Nafion, which is an ion-conductive polymer, are supported together.

When Example electrodes 1 to 5 in Example 1 are compared with Example electrodes 6 to 12 in Example 2, the Ip is almost doubled by supporting CoPyrz(CF$_3$)$_8$ together with MnO$_x$. This indicates that CoPyrz(CF$_3$)$_8$ uniformly supported on a conductive substrate serves as a 2-electron oxygen-reducing catalyst, and by supporting CoPyrz(CF$_3$)$_8$ together with MnO$_x$, which is a hydrogen peroxide decomposing catalyst, it can serve as a 4-electron oxygen-reducing catalyst in appearance.

Example 3

Preparation of Example Electrodes 13 to 16, and Comparative Example Electrodes 125 to 132

Figure 9:
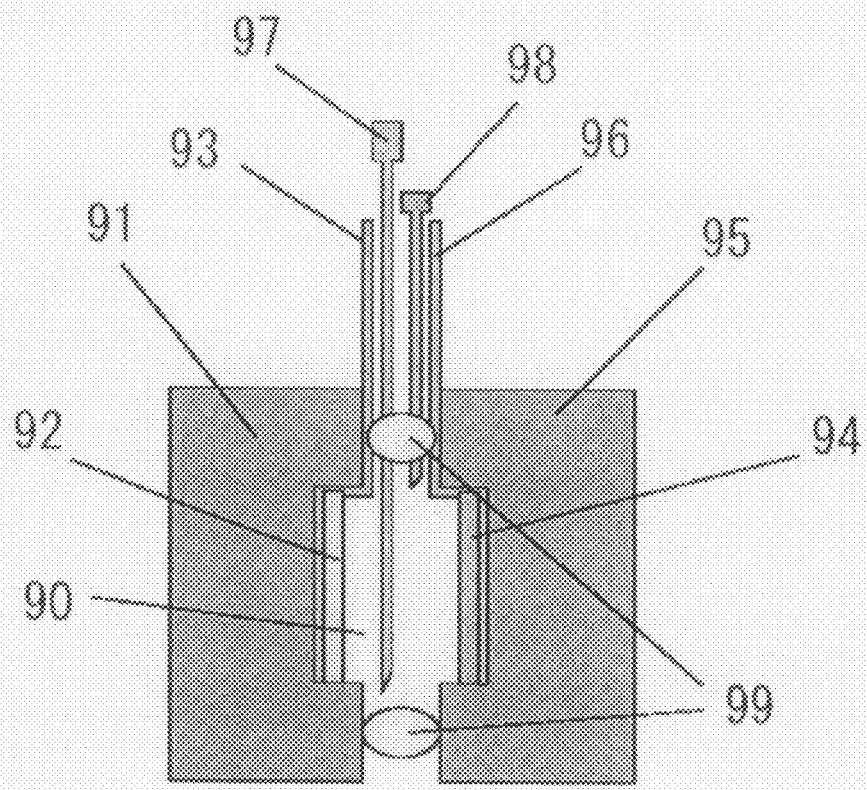
FIG. 9 is a schematic diagram showing the structure of a biofuel cell.

Each of the above electrodes has the cross-sectional structure shown in FIG. 7C. In FIG. 7C, 9 is a membrane containing Nafion, including oxygen-reducing catalysts and conductive materials (however, Example electrode 13, Comparative Example electrode 125, and Comparative Example electrode 129 do not include conductive materials).

Carbon black (CB, product of Lion Corporation, ketjen black), CNT (product of Aldrich Corporation, multi-wall carbon nanotube) or AuNano was used as a conductive material. In all electrodes, Nafion (product of Du Pont, product name: Nafion 117) was supported together with the oxygen-reducing catalyst.

Table 3 shows the catalysts and carriers (including electrode pellets) used in each oxygen-reducing electrode.

A membrane 9 containing Nafion was supported on a GC electrode pellet in the following manner. First, a mixture of ethanol and isopropyl alcohol (volumetric ratio of 1:1) was prepared, and 0.05 wt % of Nafion was dissolved in the mixture. After dispersing 1 wt % of conductive material powder in the resultant solution, an oxygen-reducing catalyst was dissolved or dispersed in the solution. 10 µl of the thus-obtained solution/dispersion was added to the GC electrode pellet dropwise followed by hot air drying for two hours. This operation was repeated 4 times, obtaining a membrane 9 containing Nafion. An oxygen-reducing electrode was thus obtained. Among the membranes 9 containing Nafion, in those containing conductive materials, the oxygen-reducing catalysts formed an agglomerate together with the conductive material.

(Evaluation of Oxygen-Reducing Properties of Electrodes)

Oxygen-reducing properties of the electrodes were evaluated in the same manner as in Example 1.

Table 3 shows the results (Ep, Ip) of Example electrodes 3 to 16, and Comparative Example electrodes 125 to 132.

TABLE 3

| Test electrode | Oxygen-reducing catalyst | Carrier | Conductive material | Ep (Volt vs Ag/AgCl) | IP (mA/cm$^2$) |
|---|---|---|---|---|---|
| Example electrode 13 | CoPyrz(CF$_3$)$_8$ | GC | — | −0.20 | 0.55 |
| Example electrode 14 | CoPyrz(CF$_3$)$_8$ | GC | CB | −0.19 | 0.62 |
| Example electrode 15 | CoPyrz(CF$_3$)$_8$ | GC | CNT | −0.19 | 0.67 |
| Example electrode 16 | CoPyrz(CF$_3$)$_8$ | GC | AuNano | −0.20 | 0.65 |
| Comp. Ex. Electrode 125 | CoPc(CN)$_8$ | GC | — | −0.25 | 0.24 |
| Comp. Ex. Electrode 126 | CoPc(CN)$_8$ | GC | CB | −0.26 | 0.28 |
| Comp. Ex. Electrode 127 | CoPc(CN)$_8$ | GC | CNT | −0.28 | 0.31 |
| Comp. Ex. Electrode 128 | CoPc(CN)$_8$ | GC | AuNano | −0.26 | 0.33 |
| Comp. Ex. Electrode 129 | CoHFPc | GC | — | −0.27 | 0.22 |
| Comp. Ex. Electrode 130 | CoHFPc | GC | CB | −0.26 | 0.26 |
| Comp. Ex. Electrode 131 | CoHFPc | GC | CNT | −0.29 | 0.30 |
| Comp. Ex. Electrode 132 | CoHFPc | GC | AuNano | −0.27 | 0.32 |

Evaluation

Because Example electrodes 13 to 16 contain CoPyrz(CF$_3$)$_8$, they can conduct oxygen reduction at a higher potential than Comparative Example electrodes 125 to 132.

Example electrode 1 wherein an oxygen-reducing catalyst was supported on a GC pellet was compared with Example electrodes 13 to 16 wherein an oxygen-reducing catalyst was supported on a GC pellet. The result was such that in Example electrodes 13 to 16 wherein CoPyrz(CF$_3$)$_8$ appeared to form agglomerates, the Ip was almost two times that of Example electrode 1. This indicates that CoPyrz(CF$_3$)$_8$ uniformly supported on a substrate functioned as a 2-electron oxygen-reducing catalyst, and CoPyrz(CF$_3$)$_8$ forming an agglomerate functioned as a four-electron reduction catalyst without the addition of a hydrogen peroxide decomposing catalyst.

Example 4

Preparation of Example Electrodes 17 to 20

Example electrodes 17 to 20 have the cross-sectional structure shown in FIG. 7D. In FIG. 7D, 10 comprises an oxygen-reducing catalyst, a hydrogen peroxide decomposing catalyst, and a conductive material, i.e., carbon black (CB), conductive substrate (CF), and Nafion (product of Du Pont, product name: Nafion 117), which is an ion-conductive polymer.

MnOOH (mixture of Mn$_3$O$_4$ and Mn$_5$O$_8$), which is a manganese oxide; a catalase, which is an enzyme; a perovskite complex oxide La$_{0.8}$Sr$_{0.2}$MnO$_3$; or brewer's yeast-activated carbon (product of Cooperative Association LATEST, product name: RAC-40, hereunder may be referred to as "RAC") was used as a hydrogen peroxide decomposing catalyst.

A CF was dipped in a hexane solution for about 5 minutes, the hexane solution being obtained by dissolving 2 wt % (about 20 mM) of CoPyrz(CF$_3$)$_8$ in hexane, followed by hot air drying for about 2 hours. A CF supporting CoPyrz(CF$_3$)$_8$ was thus obtained. The thus-obtained CF was punched into a circular plate having a diameter of 6 mm, and then placed in a guide ring 11 in such a manner as to be in contact with GC pellet 4. A mixture of ethanol and isopropyl alcohol (volumetric ratio of 1:1) was prepared, and 0.05 wt % of Nafion was dissolved in the mixture. A dispersion was prepared by dispersing 1 wt % of conductive material (CB), and adding 5 wt % of MnOOH powder, catalase, La$_{0.8}$Sr$_{0.2}$MnO$_3$ powder or RAC powder, and 200 µl of the resultant dispersion was used to impregnate the CF supporting CoPyrz(CF$_3$)$_8$ placed in the guide ring (11), followed by hot air drying for about 2 hours. Example electrodes 17 to 20 were thus obtained.

(Evaluation of Oxygen-Reducing Properties of Electrodes)

Oxygen-reducing properties of each electrode were evaluated in the same manner as in Example 1.

Table 4 shows the results (Ep, Ip) of Example electrodes 17 to 20.

TABLE 4

| Test electrode | Oxygen-reducing catalyst | Hydrogen peroxide decomposing catalyst | Carrier | Conductive material | Ep (Volt vs Ag/AgCl) | IP (mA/cm$^2$) |
|---|---|---|---|---|---|---|
| Example electrode 17 | CoPyrz(CF$_3$)$_8$ | MnOOH | CF | CB | −0.21 | 3.5 |
| Example electrode 18 | CoPyrz(CF$_3$)$_8$ | Catalase | CF | CB | −0.21 | 3.4 |
| Example electrode 19 | CoPyrz(CF$_3$)$_8$ | RAC | CF | CB | −0.18 | 4.0 |
| Example electrode 20 | CoPyrz(CF$_3$)$_8$ | La$_{0.8}$Sr$_{0.2}$MnO$_3$ | CF | CB | −0.22 | 3.2 |

Evaluation

Ep has almost no dependence on the type of the hydrogen peroxide decomposing catalyst. Ip slightly varies depending on the type of the hydrogen peroxide decomposing catalyst. In Example electrodes 17 to 20, uniformly supported CoPyrz (CF$_3$)$_8$ functioned as a 2-electron oxygen-reducing catalyst, and the hydrogen peroxide decomposing catalyst supported together with the CoPyrz(CF$_3$)$_8$ decomposed the hydrogen peroxide generated by the two-electron reduction into oxygen and water. In other words, a cycle, in which the oxygen that had been generated by decomposition of hydrogen peroxide was subjected to two-electron reduction, was repeated, and four-electron reduction was conducted in appearance. Example electrodes 17 to 20 can achieve four-electron reduction of oxygen at a higher potential by containing CoPyrz (CF$_3$)$_8$ together with a hydrogen peroxide decomposing catalyst.

Example 5

Preparation of Example Electrodes 21 and 22, and Comparative Example Electrodes 133 to 137

Each electrode was formed by using, as well as an oxygen-reducing catalyst, a 5×5 cm CP (carbon paper of Toray Industries Inc., product number: TGP-H-120, thickness of 370 μm) as a conductive substrate, a mixture of MnOOH and RAC as used in Example 4 as a hydrogen peroxide decomposing catalyst, CB as used in Example 4 as a conductive material, and Nafion as used in Example 2.

By dipping a CP into a DMF solution as used in Example 1 for about 5 minutes while stirring the solution and subjecting the CP to hot air drying, the CP was made to support 1.4 mg/cm$^2$ of CoPyrz(CF$_3$)$_8$, 3.3 mg/cm$^2$ of CoPc(CN)$_8$ or 2.8 mg/cm$^2$ of CoHFPc.

Solution 51 was prepared by dispersing 0.2 wt % of MnOOH powder and 0.5 wt % of RAC powder into a solution prepared by dissolving 0.05 wt % of Nafion in a mixture of ethanol and isopropanol at a volumetric ratio of 1:1. Solution 52 was prepared by dispersing 0.2 wt % of MnOOH powder, 0.5 wt % of RAC powder, and 0.1 wt % of CB into a solution prepared by dissolving 0.05 wt % of Nafion in a mixture of ethanol and isopropanol at a volumetric ratio of 1:1. Solution 53 was prepared by dispersing 0.1 wt % of Pt/C powder into a solution prepared by dissolving 0.05 wt % of Nafion in a mixture of ethanol and isopropanol at a volumetric ratio of 1:1.

Example electrodes 21 and 22, and Comparative Example electrodes 134 to 137 were prepared by spraying solution 51 or solution 52 onto a CP supporting CoPyrz(CF$_3$)$_8$, CoPc (CN)$_8$ or CoHFPc, followed by hot air drying for about 2 hours. The amount of Nafion supported was 1.2 to 1.6 mg/cm$^2$, the amount of MnOOH supported was about 2 mg/cm$^2$, and the amount of RAC supported was about 4 mg/cm$^2$. Comparative Example electrode 133 was prepared by spraying solution 53 onto a CP, followed by hot air drying for about 2 hours. The amount of Nafion supported was about 3 mg/cm$^2$, and the amount of Pt/C supported was about 1 mg/cm$^2$.

(Fabrication of Direct Methanol Fuel Cell (DMFC) and Property Evaluation)

0.1 wt % of PtRu/C (product of Tanaka Precious Metals Industry K.K), wherein PtRu particles are supported on carbon black, was dispersed in a solution prepared by dissolving 0.05 wt % of Nafion in a mixture of ethanol and isopropanol at a volumetric ratio of 1:1. The resultant solution was sprayed onto a CP, followed by hot air drying for about 2 hours. A fuel electrode was thus obtained.

A fuel cell (MEA) was obtained in the following manner. A fuel electrode was disposed on the center of one surface of a Nafion membrane (Nafion 112) having a size of 10×10 cm and a thickness of 0.05 mm. One of Example electrodes 21 and 22 and Comparative Example electrodes 133 to 137, which can function as an air electrode for reducing oxygen, was disposed on the center of the other surface, and the entire Nafion membrane was pressed at 130° C. for 90 seconds at 5 MPa. The thus-obtained MEA was mounted on an electrical power generation cell (product of Eiwa Corporation, standard electrical power generation cell kit: HDM-1000), a 4 volume % methanol solution was supplied to the fuel electrode at a flow rate of 14 ml/min, and the power generation properties thereof were evaluated at 65° C. Table 5 shows the output current at an open-circuit voltage and operating voltage of 0.5 V and 0.3 V.

TABLE 5

| Air electrode | Oxygen-reducing catalyst | Hydrogen peroxide decomposing catalyst | Carrier | Conductive material | Open-circuit voltage (Volt) | Output current (mA/cm²) 0.3 V | Output current (mA/cm²) 0.5 V |
|---|---|---|---|---|---|---|---|
| Example electrode 21 | CoPyrz(CF$_3$)$_8$ | MnOOH + RAC | CP | — | 0.802 | 65 | 20 |
| Example electrode 22 | CoPyrz(CF$_3$)$_8$ | MnOOH + RAC | CP | CB | 0.794 | 80 | 32 |
| Comp. Ex. electrode 133 | Pt/C | — | CP | — | 0.685 | 185 | 48 |
| Comp. Ex. electrode 134 | CoPc(CN)$_8$ | MnOOH + RAC | CP | — | 0.758 | 15 | 3 |
| Comp. Ex. electrode 135 | CoPc(CN)$_8$ | MnOOH + RAC | CP | CB | 0.755 | 18 | 7 |
| Comp. Ex. electrode 136 | CoHFPc | MnOOH + RAC | CP | — | 0.776 | 10 | 2 |
| Comp. Ex. electrode 137 | CoHFPc | MnOOH + RAC | CP | CB | 0.770 | 16 | 4 |

Evaluation

Because Example electrodes 21 and 22 contain CoPyrz (CF$_3$)$_8$, when a DMFC was formed by using Example electrodes 21 and 22 as an air electrode, a higher open-circuit voltage was obtained than when a Comparative Example electrode was used as an air electrode. The output current was smaller than a DMFC employing Comparative Example electrode 133 using Pt/C as an air electrode; the output current was several times that of the conventional cases wherein Comparative Example electrodes 134 to 137 containing cobalt phthalocyanine CoPc(CN)$_8$ or CoHFPc were used as air electrodes.

Example 6

Preparation of Example Electrodes 23 and 24, and Comparative Example Electrodes 138 to 142

Each electrode was formed by using, as well as an oxygen-reducing catalyst, a 1×1 cm CF-CNT as used in Example 1 as a conductive substrate, MnOOH as used in Example 4 as a hydrogen peroxide decomposing catalyst, CB or AuNano as used in Example 4 as a conductive material, and Nafion as used in Example 2.

A CF-CNT was dipped in a DMF solution as used in Example 1 for about 5 minutes while stirring the solution, and the CF-CNT was removed from the solution and subjected to hot-air drying. The CF-CNT was made to support 8.2 mg/cm² of CoPyrz(CF$_3$)$_8$, 14.1 mg/cm² of CoPc(CN)$_8$ or 16.3 mg/cm² of CoHFPc.

Solution 61 was prepared by dispersing 0.5 wt % of MnOOH powder into a solution that had been prepared by dissolving 0.05 wt % of Nafion in a mixture of ethanol and isopropanol at a volumetric ratio of 1:1. Solution 62 was prepared by dispersing 0.5 wt % of MnOOH powder, and 0.1 wt % of CB or AuNao into a solution that had been prepared by dissolving 0.05 wt % of Nafion in a mixture of ethanol and isopropanol at a volumetric ratio of 1:1. Solution 63 was prepared by dispersing 0.1 wt % of Pt/C powder into a solution that had been prepared by dissolving 0.05 wt % of Nafion in a mixture of ethanol and isopropanol at a volumetric ratio of 1:1.

Example electrodes 23 and 24, and Comparative Example electrodes 139 to 142 were obtained by spraying solution 61 or solution 62 onto a CF-CNT supporting CoPyrz(CF$_3$)$_8$, CoPc(CN)$_8$ or CoHFPc, followed by hot air drying for about 2 hours. The amount of Nafion supported was 6 to 11 mg/cm², and the amount of MnOOH supported was about 26 mg/cm².

Comparative Example electrode 138 was prepared by spraying the solution 63 onto CF-CNT, followed by hot air drying for about 2 hours. The amount of Nafion supported was about 8 mg/cm², and the amount of Pt/C supported was about 6 mg/cm².

(Fabrication of Biofuel Cell and Evaluation of Properties)

A 2×2 cm CF-CNT was dipped in a tetrathiafulvalene (TTF)-saturated methanol solution heated to 60° C., and the CF-CNT was removed from the solution after about 5 minutes and then dried at room temperature for 24 hours (over a whole day and night). 0.1 M phosphoric acid buffer solution containing 10 unit/μl of glucose oxidase (GOD, product of Amano Enzyme Inc., activity of 113 unit/mg) was added dropwise to the CF-CNT supporting TTF twice (250 μl each time), and the CF-CNT was then dried at room temperature for 24 hours, obtaining a glucose oxidase fuel electrode.

A biofuel cell as shown in FIG. 9 was fabricated using the thus-obtained glucose oxidase fuel electrode and an Example electrode or Comparative Example electrode as an air electrode for reducing oxygen. The glucose oxidase fuel electrode (92) was disposed in a concave portion having a size of 2×2 cm and a depth of 5 mm formed by cutting the central portion of one surface of an acrylic plate (having a size of 4×4 cm and a thickness of 1 cm) of a fuel electrode holder (91) so that the glucose oxidase fuel electrode (92) is electrically connected to a gold net (93) functioning as a current collector and an electrode reed at the negative electrode.

The air electrode (94) was disposed in a concave portion having a size of 2×2 cm and a depth of 5 mm formed by cutting the central portion of one surface of an acrylic plate (having a size of 4×4 cm and a thickness of 1 cm) of an air electrode holder (95) so that the air electrode (94) is electrically connected to a gold net (96) functioning as a current collector and an electrode reed at the negative electrode.

The fuel electrode holder (91) and the air electrode holder (95) were attached in a liquid tight manner via a fluorocarbon rubber seal ring (99) provided with a needle (97) for injecting 0.1 M phosphoric acid buffer (90) having a pH of 7.4 containing 0.1 M of glucose dissolved therein and a needle (98) for ejecting the buffer.

Table 6 shows the open-circuit voltages and the output currents at operating voltage of 0.5 V and 0.3 V of the biofuel cell.

TABLE 6

| Air electrode | Electrode catalyst | Hydrogen peroxide decomposing catalyst | Carrier | Conductive material | Open-circuit voltage (Volt) | Output current (mA/cm$^2$) 0.3 V | Output current (mA/cm$^2$) 0.5 V |
|---|---|---|---|---|---|---|---|
| Example electrode 23 | CoPyrz(CF$_3$)$_8$ | MnOOH | CF-CNT | CB | 0.820 | 5.1 | 1.8 |
| Example electrode 24 | CoPyrz(CF$_3$)$_8$ | MnOOH | CF-CNT | AuNano | 0.833 | 5.4 | 2.3 |
| Comp. Ex. electrode 138 | Pt/C | — | CF-CNT | — | 0.768 | 4.6 | 1.4 |
| Comp. Ex. electrode 139 | CoPc(CN)$_8$ | MnOOH | CF-CNT | CB | 0.802 | 2.2 | 0.7 |
| Comp. Ex. electrode 140 | CoPc(CN)$_8$ | MnOOH | CF-CNT | AuNano | 0.800 | 2.4 | 0.9 |
| Comp. Ex. electrode 141 | CoHFPc | MnOOH | CF-CNT | CB | 0.785 | 2.1 | 0.6 |
| Comp. Ex. electrode 142 | CoHFPc | MnOOH | CF-CNT | AuNano | 0.790 | 2.5 | 0.8 |

Evaluation

Because Example electrodes 23 and 24 contain CoPyrz (CF$_3$)$_8$, when biofuel cells were formed by using Example electrodes 23 and 24 as air electrodes, higher open-circuit voltages can be obtained than when a Comparative Example electrode was used as an air electrode. The output currents were almost the same as that of a biofuel cell employing Comparative Example electrode 138 using Pt/C as an air electrode. The output currents were more than two times that of fuel cells wherein Comparative Example electrodes 139 to 142 containing cobalt phthalocyanine CoPc(CN)$_8$ or CoHFPc were used as air electrodes.

Note that the same biofuel cells were fabricated using electrodes of which amount of CoPyrz(CF$_3$)$_8$ supported was less than 8.2 mg/cm$^2$, i.e., an electrode 23a (CoPyrz(CF$_3$)$_8$ supported amount=0.6 mg/cm$^2$, fabricated using a DMF solution containing 0.05 wt % of dissolved CoPyrz(CF$_3$)$_8$), an electrode 23b (CoPyrz(CF$_3$)$_8$ supported amount=2.1 mg/cm$^2$, fabricated using a DMF solution containing 0.2 wt % of dissolved CoPyrz(CF$_3$)$_8$), and an electrode 23c (CoPyrz (CF$_3$)$_8$ supported amount=4.3 mg/cm$^2$, fabricated using a DMF solution containing 0.5 wt % of dissolved CoPyrz (CF$_3$)$_8$). A biofuel cell was fabricated using an electrode of which amount of CoPyrz(CF$_3$)$_8$ supported was more than 8.2 mg/cm$^2$, i.e., electrode 23d (CoPyrz(CF$_3$)$_8$ supported amount=10.8 mg/cm$^2$, fabricated using a DMF solution containing 2.5 wt % of dissolved CoPyrz(CF$_3$)$_8$). The properties of such cells were evaluated and output currents almost the same as that of the biofuel cell fabricated using Example electrode 23 were obtained regardless of the amount of CoPyrz(CF$_3$)$_8$ supported.

In contrast, when the properties were evaluated of a biofuel cell fabricated using an electrode 138a of which amount of Pt/C supported was reduced to about 5 mg/cm$^2$, the output current was almost the same as that of a biofuel cell fabricated using an electrode 138 of which amount of Pt/C supported was about 6 mg/cm$^2$; however, a biofuel cell fabricated using an electrode 138b of which amount of Pt/C supported was reduced to about 4 mg/cm$^2$ obtained only about half the output current. Furthermore, a biofuel cell fabricated using an electrode 138b of which amount of Pt/C supported was reduced to about 2 mg/cm$^2$ obtained only one tenth the output current. Therefore, an oxygen-reducing electrode using CoPyrz(CF$_3$)$_8$ is an extremely efficient oxygen-reducing electrode, and can attain almost the same performance as an oxygen-reducing electrode using platinum with only about one tenth the amount of supporting CoPyrz(CF$_3$)$_8$.

Example 7

Fabrication of Example Electrodes 25 and 26 and Comparative Example Electrodes 143 to 147

Using a DMF solution as used in Example 1, MnOOH powder as used in Example 4 was impregnated with 2.0 wt % of oxygen-reducing catalyst.

Example electrodes 25 and 26 and Comparative Example electrodes 143 to 147 were fabricated by embedding a mixture of 2 parts by weight of impregnated MnOOH or 2 parts by weight of non-impregnated MnOOH (Comparative Example electrode 143), activated carbon powder (AC, product of Kuraray Chemical Co., Ltd., 1 part by weight of coconut shell activated carbon), 0.3 parts by weight of CB or CNT powder as used in Example 3, and 0.2 parts by weight of polytetrafluorethylene (PTFE) binder in a 20-mesh nickel-plated steel net (Ni-steel) having a thickness of 0.2 mm.

A porous Teflon (registered trademark) resin sheet having a thickness of 0.3 mm was press-fitted to one surface of the electrode, punched into a circular plate having a diameter of 10.5 mm, and used as an air electrode for a zinc-air cell.

(Fabrication of Zinc-Air Cell and Evaluation of Properties)

Circular plates of Example electrodes 25 and 26 and Comparative Example electrodes 143 to 147, which function as air electrodes, were disposed on the bottom of nickel-plated steel cell cases (diameter of 11.6 mm and a height of 5.2 mm) having a plurality of air-intake holes on the bottom in such a manner that the circular plates are in contact with the porous Teflon (registered trademark) resin sheet.

A zinc negative electrode paste, that was obtained by adding 31 wt % of aqueous potassium hydroxide solution to a mixture of a water-soluble gel polymer powder containing polyacrylic acid as a main component and zinc powder, was placed in the concave portion of a 11.2 mm of sealing plate having a sealing resin ring around its periphery, and a 10.5 mm diameter separator formed from a porous nylon sheet was then placed therein. Thereafter, the sealing plate having the zinc negative electrode paste placed therein was fitted in a cell case in such a manner that the separator was in contact with the air electrode, so that the opening of the cell case having the air electrode disposed therein was closed. The opening of the cell case was then sealed in a liquid tight manner, fabricating a zinc-air cell.

After allowing the fabricated cell to stand at 45° C. for 24 hours, open-circuit voltage and output currents were evaluated.

Cell voltage was continuously lowered from the open-circuit voltage at the rate of 1 mV/second at room temperature while measuring the current. Table 7 shows output currents at an open-circuit voltage of 1.1 V and an operating voltage of 0.9 V.

that function as air electrodes were disposed on the bottom of nickel-plated steel cell cases (diameter of 11.6 mm and height of 5.2 mm) having a plurality of air-intake holes and sugar fuel inlet/outlet holes on the bottom in such a manner that the circular plates are in contact with a porous Teflon (registered trademark) resin sheet.

A circular plate obtained by punching CF-CNT-AuNano, i.e., a carbon felt supporting carbon nanotubes and gold nanoparticles shown as in FIG. 6, into a diameter of 10 mm was placed in the concave portion of a 11.2 mm sealing plate having a sealing resin ring around its periphery.

In Example 8, a carbon felt (sold by Tsukuba Materials Information Laboratory Ltd., product number: e-4-3, carbon felt) having a thickness of 5 mm was used. The CNT and AuNano were as used in Example 1.

A separator having a diameter of 10.5 mm formed from a porous nylon sheet was then disposed. Thereafter, the sealing plate in which the zinc negative electrode paste was placed so the separator was in contact with the air electrode was fitted into the cell case in such a manner that the opening of the cell

TABLE 7

| Air electrode | Electrode catalyst | Hydrogen peroxide decomposing catalyst | Conductive carrier | material | Open-circuit voltage (Volt) | Current (mA) 0.9 V | 1.1 V |
|---|---|---|---|---|---|---|---|
| Example electrode 25 | $CoPyrz(CF_3)_8$ + AC | MnOOH | Ni-steel | CB | 1.486 | 240 | 158 |
| Example electrode 26 | $CoPyrz(CF_3)_8$ + AC | MnOOH | Ni-steel | CNT | 1.482 | 280 | 162 |
| Comp. Ex. electrode 143 | AC | MnOOH | Ni-steel | CB | 1.410 | 180 | 108 |
| Comp. Ex. electrode 144 | $CoPc(CN)_8$ + AC | MnOOH | Ni-steel | CB | 1.455 | 215 | 123 |
| Comp. Ex. electrode 145 | $CoPc(CM)_8$ + AC | MnOOH | Ni-steel | CNT | 1.485 | 210 | 126 |
| Comp. Ex. electrode 146 | CoHFPc + AC | MnOOH | Ni-steel | CB | 1.449 | 208 | 119 |
| Comp. Ex. electrode 147 | CoHFPc + AC | MnOOH | Ni-steel | CNT | 1.460 | 198 | 121 |

Evaluation

Because Example electrodes 25 and 26 contain CoPyrz $(CF_3)_8$, when zinc-air cells were formed using Example electrodes 25 and 26 as air electrodes, higher open-circuit voltages could be obtained than when Comparative Example electrodes 143 to 147 were used as air electrodes. High output currents were obtained due to the high open-circuit voltages.

Example 8

Fabrication of Sugar-Air Cell and Evaluation of Properties

Circular plates of Example electrodes 25 and 26 and Comparative Example electrodes 143 to 147 used in Example 7 case having the air electrode disposed therein was closed, and the opening of the cell case was sealed in a liquid tight manner, fabricating a sugar-air cell. About 0.4 cm³ of 0.3 M aqueous potassium hydroxide solution containing 0.2 M glucose dissolved therein was then poured through the sugar fuel inlet.

After allowing the fabricated cell to stand at 45° C. for 24 hours, open-circuit voltage and output currents were evaluated.

Cell voltage was continuously decreased from the open-circuit voltage at the rate of 1 mV/second at room temperature while measuring the current. Table 8 shows output currents at an open-circuit voltage of 0.5 V and an operating voltage of 0.3 V.

TABLE 8

| Air electrode | Electrode catalyst | Hydrogen peroxide decomposing catalyst | Carrier | Conductive material | Open-circuit voltage (Volt) | Current (mA) 0.3 V | Current (mA) 0.5 V |
|---|---|---|---|---|---|---|---|
| Example electrode 25 | CoPyrz(CF$_3$)$_8$ + AC | MnOOH | Ni-steel | CB | 0.772 | 20 | 14 |
| Example electrode 26 | CoPyrz(CF$_3$)$_8$ + AC | MnOOH | Ni-steel | CNT | 0.768 | 25 | 13 |
| Comp. Ex. electrode 143 | AC | MnOOH | Ni-steel | CB | 0.702 | 14 | 9.2 |
| Comp. Ex. electrode 144 | CoPc(CN)$_8$ + AC | MnOOH | Ni-steel | CB | 0.743 | 17 | 9.8 |
| Comp. Ex. electrode 145 | CoPc(CN)$_8$ + AC | MnOOH | Ni-steel | CNT | 0.745 | 18 | 10 |
| Comp. Ex. electrode 146 | CoHFPc + AC | MnOOH | Ni-steel | CB | 0.740 | 16 | 9.6 |
| Comp. Ex. electrode 147 | CoHFPc + AC | MnOOH | Ni-steel | CNT | 0.742 | 18 | 9.8 |

Evaluation

Because Example electrodes 25 and 26 contain CoPyrz (CF$_3$)$_8$, when sugar-air cells were formed using Example electrodes 25 and 26 as air electrodes, higher open-circuit voltages could be obtained than when Comparative Example electrodes 143 to 147 were used as air electrodes. High output currents were obtained due to the high open-circuit voltages.

The invention claimed is:

1. An oxygen-reducing electrode using a cobalt tetrapyrazinoporphyrazine derivative represented by the following Structural Formula (1) as a catalytic component

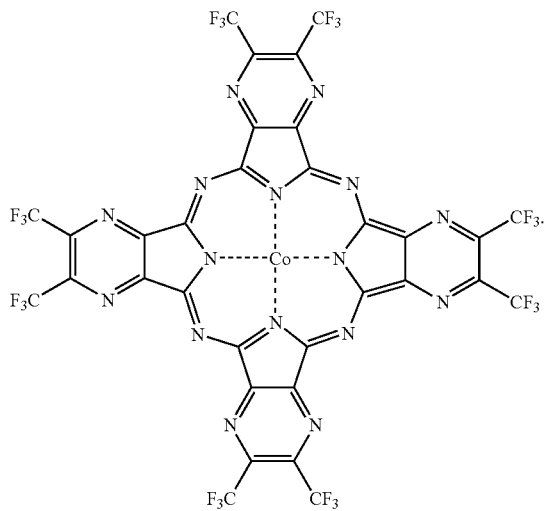

(1)

2. An oxygen-reducing electrode according to claim 1, wherein the derivative is supported on a conductive substrate.

3. An oxygen-reducing electrode according to claim 2, wherein the conductive substrate is at least one member selected from the group consisting of carbon fibers, carbon papers, carbon felts, carbon sponges, carbon nanotubes, and gold nanoparticles.

4. An oxygen-reducing electrode according to claim 1, which further comprises a hydrogen peroxide-decomposing catalyst as a catalytic component.

5. An oxygen-reducing electrode according to claim 4, wherein the hydrogen peroxide-decomposing catalyst is at least one member selected from the group consisting of manganese oxides, catalases, activated carbons, and lanthanum strontium manganese perovskite oxides.

6. An oxygen-reducing electrode according to claim 1, wherein the oxygen reduction potential is –0.2 V in a cyclic voltammogram obtained by cyclic voltammetry, the cyclic voltammetry using a three electrode cell in which the oxygen-reducing electrode is used as the working electrode, platinum is used as the counter electrode, silver/silver chloride is used as the reference electrode, and an aqueous 0.1 mol/l potassium hydroxide solution at pH 13 is used as the electrolyte.

7. An oxygen-reducing electrode according to claim 1, wherein the oxygen reduction potential is within the range of not less than –0.22 V and not more than –0.18 V in a cyclic voltammogram obtained by cyclic voltammetry, the cyclic voltammetry using a three electrode cell in which the oxygen-reducing electrode is used as the working electrode, platinum is used as the counter electrode, silver/silver chloride is used as the reference electrode, and an aqueous 0.1 mol/l potassium hydroxide solution at pH 13 is used as the electrolyte.

8. A fuel cell using a positive electrode utilizing an oxygen reduction reaction in air as a positive electrode reaction, a negative electrode utilizing an oxidation reaction of a fuel material as a negative electrode reaction, and an electrolyte, which uses the oxygen-reducing electrode of claim 1 as the positive electrode.

9. A metal-air cell using a positive electrode utilizing an oxygen reduction reaction in air as a positive electrode reaction, a negative electrode utilizing an oxidation reaction of metal as a negative electrode reaction, and an electrolyte, which uses the oxygen-reducing electrode of claim 1 as the positive electrode.

10. A sugar-air cell using a positive electrode utilizing an oxygen reduction reaction in air as a positive electrode reaction, a negative electrode utilizing an oxidation reaction of sugar as a negative electrode reaction, and an electrolyte, which uses the oxygen-reducing electrode of claim 1 as the positive electrode.

* * * * *

UNITED STATES PATENT AND TRADEMARK OFFICE
CERTIFICATE OF CORRECTION

PATENT NO. : 7,695,850 B2
APPLICATION NO. : 11/808811
DATED : April 13, 2010
INVENTOR(S) : Tadashi Sotomura et al.

Page 1 of 1

It is certified that error appears in the above-identified patent and that said Letters Patent is hereby corrected as shown below:

IN THE CLAIMS:

In column 29, line 34 (claim 1), please add a "." at the end of the claim.

1. An oxygen-reducing electrode using a cobalt tetrapyrazinoporphyrazine derivative represented by the following Structural Formula (1) as a catalytic component.

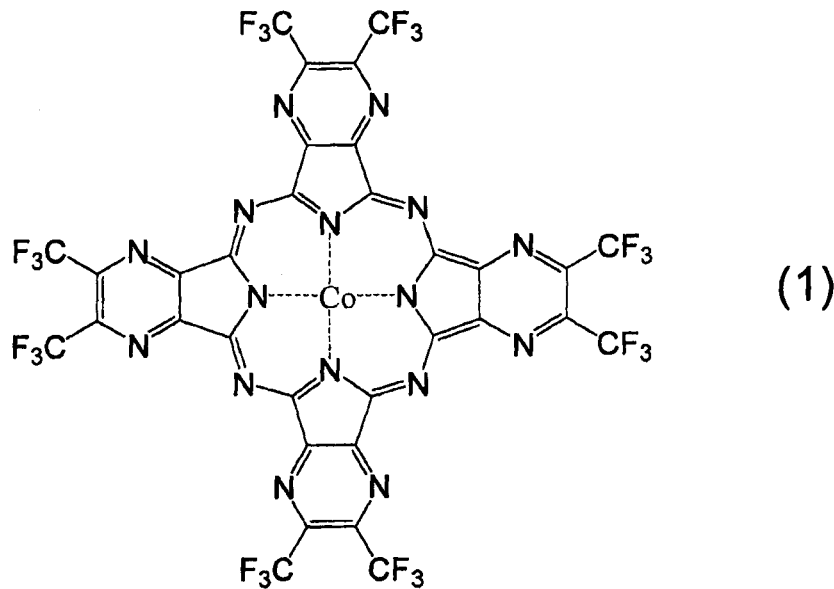

Signed and Sealed this

Twenty-third Day of November, 2010

David J. Kappos
*Director of the United States Patent and Trademark Office*